United States Patent
Shults et al.

(10) Patent No.: US 8,923,947 B2
(45) Date of Patent: Dec. 30, 2014

(54) DEVICE AND METHOD FOR DETERMINING ANALYTE LEVELS

(71) Applicant: DexCom, Inc., San Diego, CA (US)

(72) Inventors: Mark C. Shults, Madison, WI (US); Stuart J. Updike, Madison, WI (US); Rathbun K. Rhodes, Madison, WI (US); Barbara J. Gilligan, Madison, WI (US); Mark A. Tapsak, Orangeville, PA (US)

(73) Assignee: DexCom, Inc., San Diego, CA (US)

( * ) Notice: Subject to any disclaimer, the term of this patent is extended or adjusted under 35 U.S.C. 154(b) by 0 days.

(21) Appl. No.: 13/949,088

(22) Filed: Jul. 23, 2013

(65) Prior Publication Data

US 2013/0310666 A1 Nov. 21, 2013

Related U.S. Application Data

(63) Continuation of application No. 13/411,414, filed on Mar. 2, 2012, now Pat. No. 8,527,026, which is a continuation of application No. 12/696,003, filed on Jan. 28, 2010, now Pat. No. 8,155,723, which is a continuation of application No. 11/546,157, filed on Oct. 10, 2006, now abandoned, which is a continuation of application No. 11/039,269, filed on Jan. 19, 2005, now Pat. No. 7,136,689, which is a continuation of application No. 09/916,858, filed on Jul. 27, 2001, now Pat. No. 6,862,465.

(51) Int. Cl.
| | |
|---|---|
| *A61B 5/05* | (2006.01) |
| *C12Q 1/00* | (2006.01) |
| *A61B 5/1455* | (2006.01) |
| *A61B 5/1486* | (2006.01) |
| *A61B 5/00* | (2006.01) |
| *A61B 5/145* | (2006.01) |

(52) U.S. Cl.
CPC ............ *A61B 5/14532* (2013.01); *C12Q 1/006* (2013.01); *A61B 5/14558* (2013.01); *A61B 5/14865* (2013.01); *A61B 5/0031* (2013.01)

USPC .......................................... 600/345; 600/347

(58) Field of Classification Search
CPC .. A61B 5/0031; A61B 5/14532; C12Q 1/006; G01N 33/66
USPC .................. 600/309, 310, 316, 345, 347, 365
See application file for complete search history.

(56) References Cited

U.S. PATENT DOCUMENTS

| | | |
|---|---|---|
| 3,381,371 A | 5/1968 | Russell |
| 3,775,182 A | 11/1973 | Patton et al. |

(Continued)

FOREIGN PATENT DOCUMENTS

| | | |
|---|---|---|
| EP | 0 098 592 | 1/1984 |
| EP | 0 127 958 | 12/1984 |

(Continued)

OTHER PUBLICATIONS

Aalders et al. 1991. Development of a wearable glucose sensor; studies in healthy volunteers and in diabetic patients. The International Journal of Artificial Organs 14(2):102-108.

(Continued)

*Primary Examiner* — Michael D'Angelo
*Assistant Examiner* — Christian Jang
(74) *Attorney, Agent, or Firm* — Knobbe Martens Olson & Bear

(57) ABSTRACT

Devices and methods for determining analyte levels are described. The devices and methods allow for the implantation of analyte-monitoring devices, such as glucose monitoring devices that result in the delivery of a dependable flow of blood to deliver sample to the implanted device. The devices include unique architectural arrangement in the sensor region that allows accurate data to be obtained over long periods of time.

5 Claims, 7 Drawing Sheets

(56) References Cited

U.S. PATENT DOCUMENTS

| | | |
|---|---|---|
| 3,791,871 A | 2/1974 | Rowley |
| 3,838,033 A | 9/1974 | Mindt et al. |
| 3,898,984 A | 8/1975 | Mandel et al. |
| 3,943,918 A | 3/1976 | Lewis |
| 4,017,962 A * | 4/1977 | Palmer .............................. 438/65 |
| 4,197,840 A | 4/1980 | Beck et al. |
| 4,225,410 A | 9/1980 | Pace |
| 4,240,889 A | 12/1980 | Yoda et al. |
| 4,253,469 A | 3/1981 | Aslan |
| 4,255,500 A | 3/1981 | Hooke |
| 4,260,725 A | 4/1981 | Keogh et al. |
| 4,273,636 A | 6/1981 | Shimada et al. |
| 4,324,257 A | 4/1982 | Albarda et al. |
| 4,340,458 A | 7/1982 | Lerner et al. |
| 4,353,368 A | 10/1982 | Slovak et al. |
| 4,353,888 A | 10/1982 | Sefton |
| 4,374,013 A | 2/1983 | Enfors |
| 4,403,984 A | 9/1983 | Ash et al. |
| 4,418,148 A | 11/1983 | Oberhardt |
| 4,431,004 A | 2/1984 | Bessman et al. |
| 4,431,507 A | 2/1984 | Nankai et al. |
| 4,436,094 A | 3/1984 | Cerami |
| 4,442,841 A | 4/1984 | Uehara et al. |
| 4,453,537 A | 6/1984 | Spitzer |
| 4,477,314 A | 10/1984 | Richter et al. |
| 4,484,987 A | 11/1984 | Gough |
| 4,494,950 A | 1/1985 | Fischell |
| RE31,916 E | 6/1985 | Oswin et al. |
| 4,554,927 A | 11/1985 | Fussell |
| 4,571,292 A | 2/1986 | Liu et al. |
| 4,603,152 A | 7/1986 | Laurin et al. |
| 4,650,547 A | 3/1987 | Gough |
| 4,655,880 A | 4/1987 | Liu |
| 4,680,268 A | 7/1987 | Clark, Jr. |
| 4,686,044 A | 8/1987 | Behnke et al. |
| 4,703,756 A | 11/1987 | Gough et al. |
| 4,721,677 A | 1/1988 | Clark |
| 4,731,726 A | 3/1988 | Allen |
| 4,750,496 A | 6/1988 | Reinhart et al. |
| 4,757,022 A | 7/1988 | Shults et al. |
| 4,759,828 A | 7/1988 | Young et al. |
| 4,787,398 A | 11/1988 | Garcia et al. |
| 4,803,243 A | 2/1989 | Fujimoto et al. |
| 4,805,624 A | 2/1989 | Yao et al. |
| 4,805,625 A | 2/1989 | Wyler |
| 4,823,808 A | 4/1989 | Clegg et al. |
| 4,852,573 A | 8/1989 | Kennedy |
| 4,871,440 A | 10/1989 | Nagata et al. |
| 4,883,057 A | 11/1989 | Broderick |
| 4,890,620 A | 1/1990 | Gough |
| 4,890,621 A | 1/1990 | Hakky |
| 4,902,294 A | 2/1990 | Gosserez |
| 4,919,141 A | 4/1990 | Zier et al. |
| 4,927,407 A | 5/1990 | Dorman |
| 4,953,552 A | 9/1990 | DeMarzo |
| 4,970,145 A | 11/1990 | Bennetto et al. |
| 4,973,493 A | 11/1990 | Guire |
| 4,986,271 A | 1/1991 | Wilkins |
| 4,988,341 A | 1/1991 | Columbus et al. |
| 4,992,794 A | 2/1991 | Brouwers |
| 4,994,167 A | 2/1991 | Shults et al. |
| 5,002,572 A | 3/1991 | Picha |
| 5,019,096 A | 5/1991 | Fox, Jr. et al. |
| 5,034,112 A | 7/1991 | Murase et al. |
| 5,050,612 A | 9/1991 | Matsumura |
| 5,089,112 A | 2/1992 | Skotheim et al. |
| 5,108,819 A | 4/1992 | Heller et al. |
| 5,130,231 A | 7/1992 | Kennedy et al. |
| 5,137,028 A | 8/1992 | Nishimura |
| 5,160,418 A | 11/1992 | Mullen |
| 5,165,407 A | 11/1992 | Wilson et al. |
| 5,171,689 A | 12/1992 | Kawaguri et al. |
| 5,190,041 A | 3/1993 | Palti |
| 5,202,261 A | 4/1993 | Musho et al. |
| 5,222,980 A | 6/1993 | Gealow |
| 5,227,042 A | 7/1993 | Zawodzinski et al. |
| 5,249,576 A | 10/1993 | Goldberger et al. |
| 5,264,104 A | 11/1993 | Gregg et al. |
| 5,269,891 A | 12/1993 | Colin |
| 5,271,736 A | 12/1993 | Picha |
| 5,282,848 A | 2/1994 | Schmitt |
| 5,298,144 A | 3/1994 | Spokane |
| 5,299,571 A | 4/1994 | Mastrototaro |
| 5,310,469 A | 5/1994 | Cunningham et al. |
| 5,314,471 A | 5/1994 | Brauker et al. |
| 5,316,008 A | 5/1994 | Suga et al. |
| 5,321,414 A | 6/1994 | Alden et al. |
| 5,322,063 A | 6/1994 | Allen et al. |
| 5,324,322 A | 6/1994 | Grill, Jr. et al. |
| 5,328,451 A | 7/1994 | Davis et al. |
| 5,331,555 A | 7/1994 | Hashimoto et al. |
| 5,334,681 A | 8/1994 | Mueller et al. |
| 5,337,747 A | 8/1994 | Neftel |
| 5,344,454 A | 9/1994 | Clarke et al. |
| 5,352,351 A | 10/1994 | White |
| 5,368,028 A | 11/1994 | Palti |
| 5,372,133 A | 12/1994 | Hogen Esch |
| 5,380,536 A | 1/1995 | Hubbell et al. |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney, II et al. |
| 5,411,647 A | 5/1995 | Johnson et al. |
| 5,411,866 A | 5/1995 | Luong |
| 5,417,395 A | 5/1995 | Fowler et al. |
| 5,421,923 A | 6/1995 | Clarke et al. |
| 5,429,735 A | 7/1995 | Johnson et al. |
| 5,431,160 A | 7/1995 | Wilkins |
| 5,431,921 A | 7/1995 | Thombre |
| 5,453,278 A | 9/1995 | Chan et al. |
| 5,458,631 A | 10/1995 | Xavier et al. |
| 5,462,064 A | 10/1995 | D'Angelo et al. |
| 5,462,645 A | 10/1995 | Albery et al. |
| 5,464,013 A | 11/1995 | Lemelson |
| 5,466,356 A | 11/1995 | Schneider et al. |
| 5,469,846 A | 11/1995 | Khan |
| 5,476,094 A | 12/1995 | Allen et al. |
| 5,480,711 A | 1/1996 | Ruefer |
| 5,482,008 A | 1/1996 | Stafford et al. |
| 5,494,562 A | 2/1996 | Maley et al. |
| 5,497,772 A | 3/1996 | Schulman et al. |
| 5,507,288 A | 4/1996 | Bocker et al. |
| 5,508,030 A | 4/1996 | Bierman |
| 5,508,509 A | 4/1996 | Yafuso et al. |
| 5,513,636 A | 5/1996 | Palti |
| 5,518,601 A | 5/1996 | Foos et al. |
| 5,529,066 A | 6/1996 | Palti |
| 5,531,878 A | 7/1996 | Vadgama et al. |
| 5,538,511 A | 7/1996 | Van Antwerp |
| 5,545,223 A | 8/1996 | Neuenfeldt et al. |
| 5,549,675 A | 8/1996 | Neuenfeldt et al. |
| 5,564,439 A | 10/1996 | Picha |
| 5,568,806 A | 10/1996 | Cheney, II et al. |
| 5,569,186 A | 10/1996 | Lord et al. |
| 5,569,462 A | 10/1996 | Martinson et al. |
| 5,571,395 A | 11/1996 | Park et al. |
| 5,575,930 A | 11/1996 | Tietje-Girault et al. |
| 5,578,463 A | 11/1996 | Berka et al. |
| 5,582,184 A | 12/1996 | Erickson et al. |
| 5,582,697 A | 12/1996 | Ikeda et al. |
| 5,584,813 A | 12/1996 | Livingston et al. |
| 5,586,553 A | 12/1996 | Halili et al. |
| 5,589,133 A | 12/1996 | Suzuki |
| 5,589,498 A | 12/1996 | Mohr et al. |
| 5,593,440 A | 1/1997 | Brauker et al. |
| 5,593,852 A | 1/1997 | Heller et al. |
| 5,607,565 A | 3/1997 | Azarnia et al. |
| 5,628,890 A | 5/1997 | Carter et al. |
| 5,640,954 A | 6/1997 | Pfeiffer |
| 5,653,756 A | 8/1997 | Clarke et al. |
| 5,653,863 A | 8/1997 | Genshaw et al. |
| 5,660,163 A | 8/1997 | Schulman et al. |
| 5,686,829 A | 11/1997 | Girault |
| 5,695,623 A | 12/1997 | Michel et al. |

(56) References Cited

U.S. PATENT DOCUMENTS

| | | |
|---|---|---|
| 5,704,354 A | 1/1998 | Priedel et al. |
| 5,706,807 A | 1/1998 | Picha |
| 5,711,861 A | 1/1998 | Ward et al. |
| 5,713,888 A | 2/1998 | Neuenfeldt et al. |
| 5,733,336 A | 3/1998 | Neuenfeldt et al. |
| 5,735,273 A | 4/1998 | Kurnik et al. |
| 5,741,319 A | 4/1998 | Woloszko et al. |
| 5,741,330 A | 4/1998 | Brauker et al. |
| 5,743,262 A | 4/1998 | Lepper, Jr. et al. |
| 5,771,890 A | 6/1998 | Tamada |
| 5,776,324 A | 7/1998 | Usala |
| 5,777,060 A | 7/1998 | Van Antwerp |
| 5,782,912 A | 7/1998 | Brauker et al. |
| 5,791,344 A | 8/1998 | Schulman et al. |
| 5,800,420 A | 9/1998 | Gross |
| 5,800,529 A | 9/1998 | Brauker et al. |
| 5,804,048 A | 9/1998 | Wong et al. |
| 5,807,375 A | 9/1998 | Gross et al. |
| 5,807,406 A | 9/1998 | Brauker et al. |
| 5,820,622 A | 10/1998 | Gross et al. |
| 5,833,603 A | 11/1998 | Kovacs et al. |
| 5,837,728 A | 11/1998 | Purcell |
| 5,840,148 A | 11/1998 | Campbell et al. |
| 5,863,400 A | 1/1999 | Drummond et al. |
| 5,882,354 A | 3/1999 | Brauker et al. |
| 5,882,494 A | 3/1999 | Van Antwerp |
| 5,895,235 A | 4/1999 | Droz |
| 5,906,817 A | 5/1999 | Moullier et al. |
| 5,914,026 A | 6/1999 | Blubaugh et al. |
| 5,931,814 A | 8/1999 | Alex et al. |
| 5,944,661 A | 8/1999 | Swette et al. |
| 5,957,854 A | 9/1999 | Besson et al. |
| 5,961,451 A | 10/1999 | Reber et al. |
| 5,963,132 A | 10/1999 | Yoakum |
| 5,964,261 A | 10/1999 | Neuenfeldt et al. |
| 5,964,993 A | 10/1999 | Blubaugh et al. |
| 5,967,986 A | 10/1999 | Cimochowski et al. |
| 5,985,129 A | 11/1999 | Gough et al. |
| 5,989,409 A | 11/1999 | Kurnik et al. |
| 6,001,067 A | 12/1999 | Shults et al. |
| 6,011,984 A | 1/2000 | Van Antwerp et al. |
| 6,013,113 A | 1/2000 | Mika |
| 6,049,727 A | 4/2000 | Crothall |
| 6,059,946 A | 5/2000 | Yukawa et al. |
| 6,066,083 A | 5/2000 | Slater et al. |
| 6,066,448 A | 5/2000 | Wohlstadter et al. |
| 6,074,775 A | 6/2000 | Gartstein et al. |
| 6,081,736 A | 6/2000 | Colvin et al. |
| 6,088,608 A | 7/2000 | Schulman et al. |
| 6,091,975 A | 7/2000 | Daddona et al. |
| 6,093,172 A | 7/2000 | Funderburk et al. |
| 6,117,290 A | 9/2000 | Say et al. |
| 6,119,028 A | 9/2000 | Schulman et al. |
| 6,122,536 A | 9/2000 | Sun et al. |
| 6,134,461 A | 10/2000 | Say et al. |
| 6,144,869 A | 11/2000 | Berner et al. |
| 6,144,871 A | 11/2000 | Saito et al. |
| 6,175,752 B1 | 1/2001 | Say et al. |
| 6,180,416 B1 | 1/2001 | Kurnik et al. |
| 6,190,326 B1 | 2/2001 | McKinnon et al. |
| 6,200,772 B1 | 3/2001 | Vadgama et al. |
| 6,201,980 B1 | 3/2001 | Darrow et al. |
| 6,208,894 B1 | 3/2001 | Schulman et al. |
| 6,212,416 B1 | 4/2001 | Ward et al. |
| 6,223,080 B1 | 4/2001 | Thompson |
| 6,223,083 B1 | 4/2001 | Rosar |
| 6,230,059 B1 | 5/2001 | Duffin |
| 6,233,471 B1 | 5/2001 | Berner et al. |
| 6,254,586 B1 | 7/2001 | Mann et al. |
| 6,256,522 B1 | 7/2001 | Schultz |
| 6,259,937 B1 | 7/2001 | Schulman et al. |
| 6,264,825 B1 | 7/2001 | Blackburn et al. |
| 6,268,161 B1 | 7/2001 | Han et al. |
| 6,272,364 B1 | 8/2001 | Kurnik |
| 6,272,382 B1 | 8/2001 | Faltys et al. |
| 6,275,717 B1 | 8/2001 | Gross et al. |
| 6,285,897 B1 | 9/2001 | Kilcoyne et al. |
| 6,296,615 B1 | 10/2001 | Brockway et al. |
| 6,299,578 B1 | 10/2001 | Kurnik et al. |
| 6,300,002 B1 | 10/2001 | Webb et al. |
| 6,304,788 B1 | 10/2001 | Eady et al. |
| 6,309,351 B1 | 10/2001 | Kurnik et al. |
| 6,309,526 B1 | 10/2001 | Fujiwara et al. |
| 6,315,719 B1 | 11/2001 | Rode et al. |
| 6,325,979 B1 | 12/2001 | Hahn et al. |
| 6,326,160 B1 | 12/2001 | Dunn et al. |
| 6,329,161 B1 | 12/2001 | Heller et al. |
| 6,330,464 B1 * | 12/2001 | Colvin et al. .................. 600/316 |
| 6,336,900 B1 | 1/2002 | Alleckson et al. |
| 6,343,225 B1 | 1/2002 | Clark, Jr. |
| 6,360,888 B1 | 3/2002 | McIvor et al. |
| 6,366,794 B1 | 4/2002 | Moussy et al. |
| 6,368,274 B1 | 4/2002 | Van Antwerp et al. |
| 6,400,974 B1 | 6/2002 | Lesho |
| 6,405,066 B1 | 6/2002 | Essenpreis et al. |
| 6,406,066 B1 | 6/2002 | Uegane |
| 6,406,426 B1 | 6/2002 | Reuss et al. |
| 6,409,674 B1 | 6/2002 | Brockway et al. |
| 6,424,847 B1 | 7/2002 | Mastrototaro et al. |
| 6,442,413 B1 | 8/2002 | Silver |
| 6,447,448 B1 | 9/2002 | Ishikawa et al. |
| 6,454,710 B1 | 9/2002 | Ballerstadt et al. |
| 6,466,810 B1 | 10/2002 | Ward et al. |
| 6,484,046 B1 | 11/2002 | Say et al. |
| 6,497,729 B1 | 12/2002 | Moussy et al. |
| 6,512,939 B1 | 1/2003 | Colvin et al. |
| 6,528,584 B2 | 3/2003 | Kennedy et al. |
| 6,534,711 B1 | 3/2003 | Pollack |
| 6,546,268 B1 | 4/2003 | Ishikawa et al. |
| 6,547,839 B2 | 4/2003 | Zhang et al. |
| 6,558,320 B1 | 5/2003 | Causey et al. |
| 6,558,321 B1 | 5/2003 | Burd et al. |
| 6,565,509 B1 | 5/2003 | Say et al. |
| 6,569,309 B2 | 5/2003 | Otsuka et al. |
| 6,587,705 B1 | 7/2003 | Kim et al. |
| 6,591,125 B1 | 7/2003 | Buse et al. |
| 6,618,934 B1 | 9/2003 | Feldman et al. |
| 6,666,821 B2 | 12/2003 | Keimel |
| 6,699,383 B2 | 3/2004 | Lemire et al. |
| 6,702,857 B2 | 3/2004 | Brauker et al. |
| 6,702,972 B1 | 3/2004 | Markle |
| 6,721,587 B2 | 4/2004 | Gough |
| 6,737,158 B1 | 5/2004 | Thompson |
| 6,741,877 B1 | 5/2004 | Shults et al. |
| 6,773,565 B2 | 8/2004 | Kunimoto et al. |
| 6,793,632 B2 | 9/2004 | Sohrab |
| 6,793,802 B2 | 9/2004 | Lee et al. |
| 6,804,544 B2 | 10/2004 | van Antwerp et al. |
| 6,862,465 B2 | 3/2005 | Shults et al. |
| 6,895,263 B2 | 5/2005 | Shin et al. |
| 6,936,006 B2 | 8/2005 | Sabra |
| 6,952,604 B2 | 10/2005 | DeNuzzio et al. |
| 6,965,791 B1 | 11/2005 | Hitchcock et al. |
| 6,972,080 B1 | 12/2005 | Tomioka et al. |
| 6,991,643 B2 | 1/2006 | Saadat |
| 7,058,437 B2 | 6/2006 | Buse et al. |
| 7,074,307 B2 | 7/2006 | Simpson et al. |
| 7,081,195 B2 | 7/2006 | Simpson et al. |
| 7,108,778 B2 | 9/2006 | Simpson et al. |
| 7,110,803 B2 | 9/2006 | Shults et al. |
| 7,115,884 B1 | 10/2006 | Walt et al. |
| 7,134,999 B2 | 11/2006 | Brauker et al. |
| 7,136,689 B2 | 11/2006 | Shults et al. |
| 7,153,265 B2 | 12/2006 | Vachon |
| 7,166,074 B2 | 1/2007 | Reghabit et al. |
| 7,169,289 B2 | 1/2007 | Schulein et al. |
| 7,192,450 B2 | 3/2007 | Brauker et al. |
| 7,225,535 B2 | 6/2007 | Feldman et al. |
| 7,329,239 B2 | 2/2008 | Safabash et al. |
| 7,344,499 B1 | 3/2008 | Prausnitz et al. |
| 7,364,592 B2 | 4/2008 | Carr-Brendel et al. |
| 7,404,819 B1 | 7/2008 | Darios et al. |
| 7,417,164 B2 | 8/2008 | Suri |
| 7,426,408 B2 | 9/2008 | DeNuzzio et al. |

(56) References Cited

U.S. PATENT DOCUMENTS

| | | |
|---|---|---|
| 7,471,972 B2 | 12/2008 | Rhodes et al. |
| 7,583,990 B2 | 9/2009 | Goode, Jr. et al. |
| 7,632,228 B2 | 12/2009 | Brauker et al. |
| 7,657,297 B2 | 2/2010 | Simpson et al. |
| 7,711,402 B2 | 5/2010 | Shults et al. |
| 7,792,562 B2 | 9/2010 | Shults et al. |
| 7,835,777 B2 | 11/2010 | Shults et al. |
| 7,860,545 B2 | 12/2010 | Shults et al. |
| 7,970,448 B2 | 6/2011 | Shults et al. |
| 7,974,672 B2 | 7/2011 | Shults et al. |
| 8,155,723 B2 | 4/2012 | Shults et al. |
| 8,527,025 B1 | 9/2013 | Shults et al. |
| 2002/0042090 A1 | 4/2002 | Heller et al. |
| 2002/0042561 A1 | 4/2002 | Schulman et al. |
| 2002/0055673 A1 | 5/2002 | Van Antwerp et al. |
| 2002/0151816 A1 | 10/2002 | Rich et al. |
| 2002/0169369 A1 | 11/2002 | Ward et al. |
| 2002/0188185 A1 | 12/2002 | Sohrab |
| 2003/0006669 A1 | 1/2003 | Pei et al. |
| 2003/0023317 A1 | 1/2003 | Brauker et al. |
| 2003/0032874 A1 | 2/2003 | Rhodes et al. |
| 2003/0036773 A1 | 2/2003 | Whitehurst et al. |
| 2003/0059631 A1 | 3/2003 | Al-Lamee |
| 2003/0065254 A1 | 4/2003 | Schulman et al. |
| 2003/0070548 A1 | 4/2003 | Clausen |
| 2003/0125613 A1 | 7/2003 | Enegren et al. |
| 2003/0130616 A1 | 7/2003 | Steil et al. |
| 2003/0134347 A1 | 7/2003 | Heller et al. |
| 2003/0138674 A1 | 7/2003 | Zeikus et al. |
| 2003/0181794 A1 | 9/2003 | Rini et al. |
| 2003/0187338 A1 | 10/2003 | Say et al. |
| 2003/0199744 A1 | 10/2003 | Buse et al. |
| 2003/0199745 A1 | 10/2003 | Burson et al. |
| 2003/0211625 A1 | 11/2003 | Cohan |
| 2003/0225361 A1 | 12/2003 | Sabra |
| 2003/0235817 A1 | 12/2003 | Bartkowiak et al. |
| 2004/0011671 A1 | 1/2004 | Shults et al. |
| 2004/0015063 A1 | 1/2004 | DeNuzzio et al. |
| 2004/0018486 A1 | 1/2004 | Dunn et al. |
| 2004/0087671 A1 | 5/2004 | Tamada et al. |
| 2004/0106857 A1 | 6/2004 | Gough |
| 2004/0143173 A1 | 7/2004 | Reghabi et al. |
| 2004/0158138 A1 | 8/2004 | Kilcoyne et al. |
| 2004/0167801 A1 | 8/2004 | Say et al. |
| 2004/0186362 A1 | 9/2004 | Brauker et al. |
| 2005/0008671 A1 | 1/2005 | Van Antwerp |
| 2005/0033132 A1 | 2/2005 | Shults et al. |
| 2005/0051427 A1 | 3/2005 | Brauker et al. |
| 2005/0051440 A1 | 3/2005 | Simpson et al. |
| 2005/0056552 A1 | 3/2005 | Simpson et al. |
| 2005/0059871 A1 | 3/2005 | Gough et al. |
| 2005/0096519 A1 | 5/2005 | DeNuzzio et al. |
| 2005/0103625 A1 | 5/2005 | Rhodes et al. |
| 2005/0112169 A1 | 5/2005 | Brauker et al. |
| 2005/0121322 A1 | 6/2005 | Say et al. |
| 2005/0124873 A1 | 6/2005 | Shults et al. |
| 2005/0139489 A1 | 6/2005 | Davies et al. |
| 2005/0143635 A1 | 6/2005 | Kamath et al. |
| 2005/0177036 A1 | 8/2005 | Shults et al. |
| 2005/0181012 A1 | 8/2005 | Saint et al. |
| 2005/0182451 A1 | 8/2005 | Griffin et al. |
| 2005/0211571 A1 | 9/2005 | Schulein et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0251083 A1 | 11/2005 | Carr-Brendel et al. |
| 2005/0271546 A1 | 12/2005 | Gerber et al. |
| 2005/0272989 A1 | 12/2005 | Shah et al. |
| 2006/0015020 A1 | 1/2006 | Neale et al. |
| 2006/0016700 A1 | 1/2006 | Brister et al. |
| 2006/0189856 A1 | 8/2006 | Petisce et al. |
| 2006/0200022 A1 | 9/2006 | Brauker et al. |
| 2006/0211921 A1 | 9/2006 | Brauker et al. |
| 2006/0222566 A1 | 10/2006 | Brauker et al. |
| 2006/0224108 A1 | 10/2006 | Brauker et al. |
| 2006/0257995 A1 | 11/2006 | Simpson et al. |
| 2006/0257996 A1 | 11/2006 | Simpson et al. |
| 2006/0263763 A1 | 11/2006 | Simpson et al. |
| 2006/0270922 A1 | 11/2006 | Brauker et al. |
| 2006/0270923 A1 | 11/2006 | Brauker et al. |
| 2006/0281985 A1 | 12/2006 | Ward et al. |
| 2007/0027370 A1 | 2/2007 | Brauker et al. |
| 2007/0032718 A1 | 2/2007 | Shults et al. |
| 2007/0045902 A1 | 3/2007 | Brauker et al. |
| 2007/0173711 A1 | 7/2007 | Shah et al. |
| 2007/0203966 A1 | 8/2007 | Brauker et al. |
| 2007/0235331 A1 | 10/2007 | Simpson et al. |
| 2007/0259217 A1 | 11/2007 | Logan |
| 2008/0021666 A1 | 1/2008 | Goode et al. |
| 2008/0045824 A1 | 2/2008 | Tapsak et al. |
| 2008/0154101 A1 | 6/2008 | Jain et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262334 A1 | 10/2008 | Dunn et al. |
| 2008/0296155 A1 | 12/2008 | Shults et al. |
| 2008/0305009 A1 | 12/2008 | Gamsey et al. |
| 2008/0305506 A1 | 12/2008 | Suri |
| 2008/0306368 A1 | 12/2008 | Goode et al. |
| 2009/0018418 A1 | 1/2009 | Markle et al. |
| 2009/0018426 A1 | 1/2009 | Markle et al. |
| 2009/0030297 A1 | 1/2009 | Miller et al. |
| 2009/0036763 A1 | 2/2009 | Brauker et al. |
| 2009/0045055 A1 | 2/2009 | Rhodes et al. |
| 2009/0061528 A1 | 3/2009 | Suri |
| 2009/0062633 A1 | 3/2009 | Brauker et al. |
| 2009/0081803 A1 | 3/2009 | Gamsey et al. |
| 2009/0177143 A1 | 7/2009 | Markle et al. |
| 2009/0264719 A1 | 10/2009 | Markle et al. |
| 2010/0087724 A1 | 4/2010 | Brauker et al. |
| 2010/0099970 A1 | 4/2010 | Shults et al. |
| 2010/0099971 A1 | 4/2010 | Shults et al. |
| 2010/0160760 A1 | 6/2010 | Shults et al. |
| 2010/0204555 A1 | 8/2010 | Shults et al. |
| 2010/0204559 A1 | 8/2010 | Shults et al. |
| 2010/0256779 A1 | 10/2010 | Brauker et al. |
| 2011/0253533 A1 | 10/2011 | Shults et al. |
| 2012/0179014 A1 | 7/2012 | Shults et al. |

FOREIGN PATENT DOCUMENTS

| | | |
|---|---|---|
| EP | 0 286 118 | 10/1988 |
| EP | 0 320 109 | 6/1989 |
| EP | 0 353 328 | 2/1990 |
| EP | 0 390 390 | 10/1990 |
| EP | 0 396 788 | 11/1990 |
| EP | 0 534 074 | 3/1993 |
| EP | 0 539 625 | 5/1993 |
| EP | 0 563 795 | 10/1993 |
| EP | 0 647 849 | 4/1995 |
| EP | 0 967 788 | 12/1999 |
| FR | 2656423 | 6/1991 |
| FR | 2760962 | 9/1998 |
| GB | 2149918 | 6/1985 |
| JP | 62083649 | 4/1987 |
| JP | 02002913 | 1/1990 |
| JP | 3-293556 | 12/1991 |
| JP | 2002-189015 | 7/2002 |
| WO | WO 89/02720 | 4/1989 |
| WO | WO 90/00738 | 1/1990 |
| WO | WO 91/09302 | 6/1991 |
| WO | WO 92/07525 | 5/1992 |
| WO | WO 92/13271 | 8/1992 |
| WO | WO 93/14693 | 8/1993 |
| WO | WO 93/19701 | 10/1993 |
| WO | WO 94/22367 | 10/1994 |
| WO | WO 96/01611 | 1/1996 |
| WO | WO 96/14026 | 5/1996 |
| WO | WO 96/25089 | 8/1996 |
| WO | WO 96/32076 | 10/1996 |
| WO | WO 96/36296 | 11/1996 |

(56) References Cited

FOREIGN PATENT DOCUMENTS

| | | |
|---|---|---|
| WO | WO 97/01986 | 1/1997 |
| WO | WO 97/43633 | 11/1997 |
| WO | WO 98/24358 | 6/1998 |
| WO | WO 98/38906 | 9/1998 |
| WO | WO 99/56613 | 4/1999 |
| WO | WO 00/13003 | 3/2000 |
| WO | WO 00/19887 | 4/2000 |
| WO | WO 00/32098 | 6/2000 |
| WO | WO 00/33065 | 6/2000 |
| WO | WO 00/59373 | 10/2000 |
| WO | WO 00/74753 | 12/2000 |
| WO | WO 01/12158 | 2/2001 |
| WO | WO 01/20019 | 3/2001 |
| WO | WO 01/20334 | 3/2001 |
| WO | WO 01/34243 | 5/2001 |
| WO | WO 01/43660 | 6/2001 |
| WO | WO 01/68901 | 9/2001 |
| WO | WO 01/69222 | 9/2001 |
| WO | WO 01/88524 | 11/2001 |
| WO | WO 01/88534 | 11/2001 |
| WO | WO 2005/012873 | 2/2005 |
| WO | WO 2005/057168 | 6/2005 |
| WO | WO 2005/026689 | 10/2005 |

OTHER PUBLICATIONS

Abe et al. 1992. Characterization of glucose microsensors for intracellular measurements. Anal. Chem. 64(18):2160-2163.
Abel et al. 1984. Experience with an implantable glucose sensor as a prerequisite of an artificial beta cell, Biomed. Biochim. Acta 43(5):577-584.
Abel et al. 2002. Biosensors for in vivo glucose measurement: can we cross the experimental stage. Biosens Bioelectron 17:1059-1070.
Alcock & Turner. 1994. Continuous Analyte Monitoring to Aid Clinical Practice. IEEE Engineering in Med. & Biol. Mag. 13:319-325.
American Heritage Dictionary, 4th Edition. 2000. Houghton Mifflin Company, p. 82.
Amin et al. 2003. Hypoglycemia prevalence in prepubertal children with type 1 diabetes on standard insulin regimen: Use of continuous glucose monitoring system. Diabetes Care 26(3):662-667.
Answers.com. "xenogenic." The American Heritage Stedman's Medical Dictionary. Houghton Mifflin Company, 2002. Answers.com Nov. 7, 2006 http://www.Answers.com/topic/xenogenic.
Armour et al. Dec. 1990. Application of Chronic Intravascular Blood Glucose Sensor in Dogs. Diabetes 39:1519-1526.
Asberg et al. 2003. Hydrogels of a Conducting Conjugated Polymer as 3-D Enzyme Electrode. Biosensors Bioelectronics. pp. 199-207.
Atanasov et al. 1994. Biosensor for continuous glucose monitoring. Biotechnology and Bioengineering 43:262-266.
Atanasov et al. 1997. Implantation of a refillable glucose monitoring-telemetry device. Biosens Bioelectron 12:669-680.
Aussedat et al. 1997. A user-friendly method for calibrating a subcutaneous glucose sensor-based hypoglycaemic alarm. Biosensors & Bioelectronics 12(11):1061-1071.
Bailey et al. 2007. Reduction in hemoglobin A1c with real-time continuous glucose monitoring: results from a 12-week observational study. Diabetes Technology & Therapeutics 9(3):203-210.
Baker et al. 1996. Dynamic delay and maximal dynamic error in continuous biosensors. Anal Chem 68(8):1292-1297.
Bard et al. 1980. Electrochemical Methods. John Wiley & Sons, pp. 173-175.
Beach et al. 1999. Subminiature implantable potentiostat and modified commercial telemetry device for remote glucose monitoring. IEEE Transactions on Instrumentation and Measurement 48(6):1239-1245.
Bellucci et al. Jan. 1986. Electrochemical behaviour of graphite-epoxy composite materials (GECM) in aqueous salt solutions, Journal of Applied Electrochemistry, 16(1):15-22.
Bessman et al., Progress toward a glucose sensor for the artificial pancreas, Proceedings of a Workshop on Ion-Selective Microelectrodes, Jun. 4-5, 1973, Boston, MA, 189-197.

Biermann et al. 2008. How would patients behave if they were continually informed of their blood glucose levels? A simulation study using a "virtual" patient. Diab. Thechnol. & Therapeut., 10:178-187.
Bindra et al. 1989. Pulsed amperometric detection of glucose in biological fluids at a surface-modified gold electrode. Anal Chem 61:2566-2570.
Bindra et al. 1991. Design and In Vitro Studies of a Needle-Type Glucose Senso for Subcutaneous Monitoring. Anal. Chem 63:1692-96.
Bisenberger et al. 1995. A triple-step potential waveform at enzyme multisensors with thick-film gold electrodes for detection of glucose and sucrose. Sensors and Actuators, B 28:181-189.
Bland et al. 1990. A note on the use of the intraclass correlation coefficient in the evaluation of agreement between two methods of measurement. Comput. Biol. Med. 20(5):337-340.
Bobbioni-Harsch et al. 1993. Lifespan of subcutaneous glucose sensors and their performances during dynamic glycaemia changes in rats, J. Biomed. Eng. 15:457-463.
Bode et al. 1999. Continuous glucose monitoring used to adjust diabetes therapy improves glycosylated hemoglobin: A pilot study. Diabetes Research and Clinical Practice 46:183-190.
Bode et al. 2000. Using the continuous glucose monitoring system to improve the management of type 1 diabetes. Diabetes Technology & Therapeutics, 2(Suppl 1):S43-48.
Bode, B. W. 2000. Clinical utility of the continuous glucose monitoring system. Diabetes Technol Ther, 2(Suppl 1):535-41.
Boedeker Plastics, Inc. 2009. Polyethylene Specifications Data Sheet, http://www.boedeker.com/polye_p.htm [Aug. 19, 2009 3:36:33 PM].
Boland et al. 2001. Limitations of conventional methods of self-monitoring of blood glucose. Diabetes Care 24(11):1858-1862.
Bott, A. W. 1997. A Comparison of Cyclic Voltammetry and Cyclic Staircase Voltammetry Current Separations 16:1, 23-26.
Bowman et al. 1986. The packaging of implantable integrated sensors. IEEE Trans Biomed Eng BME33(2):248-255.
Brauker et al. 1995. Neovascularization of synthetic membranes directed by membrane Microarchitecture. J. Biomed Mater Res 29:1517-1524.
Brauker et al. 1996. Local Inflammatory Response Around Diffusion Chambers Containing Xenografts Transplantation 61(12):1671-1677.
Brauker et al. 1998. Sustained expression of high levels of human factor IX from human cells implanted within an immunoisolation device into athymic rodents. Hum Gene Ther 9:879-888.
Brauker et al. 2001. Unraveling Mysteries at the Biointerface: Molecular Mediator of Inhibition of Blood vessel Formation in the Foreign Body Capsule Revealed. Surfacts Biomaterials 6. 1;5.
Braunwald, 2008. Biomarkers in heart failure. N. Engl. J. Med., 358: 2148-2159.
Bremer et al. 2001. Benchmark data from the literature for evaluation of new glucose sensing technologies. Diabetes Technology & Therapeutics 3(3):409-418.
Brooks et al. "Development of an on-line glucose sensor for fermentation monitoring," Biosensors, 3:45-56 (1987/88).
Bruckel et al. 1989. In vivo measurement of subcutaneous glucose concentrations with an enzymatic glucose sensor and a wick method. Klin Wochenschr 67:491-495.
Brunner et al. 1998. Validation of home blood glucose meters with respect to clinical and analytical approaches. Diabetes Care 21(4):585-590.
Cai et al. 2004. A wireless, remote query glucose biosensor based on a pH-sensitive polymer. Anal Chem 76(4):4038-4043.
Campanella et al. 1993. Biosensor for direct determination of glucose and lactate in undiluted biological fluids. Biosensors & Bioelectronics 8:307-314.
Candas et al (1994). "An adaptive plasma glucose controller basedon on a nonlinear insulin/glucose model." IEEE Transactions on Biomedical Engineering, 41(2): 116-124.
Cass et al. "Ferrocene-mediated enzyme electrodes for amperometric determination of glucose," Anal. Chem., 36:667-71 (1984).
Cassidy et al., Apr. 1993. Novel electrochemical device for the detection of cholesterol or glucose, Analyst, 118:415-418.

(56) References Cited

OTHER PUBLICATIONS

Cellulose Acetate Product Description, Apr. 7, 2005, Product No. 419028, Sigma-Aldrich Corp., St. Louis, MO.
Chase et al. 2001. Continuous subcutaneous glucose monitoring in children with type 1 diabetes. Pediatrics 107:222-226.
Chatterjee et al. 1997. Poly(ether Urethane) and poly(ether urethane urea) membranes with high H2S/CH4 selectivity, Journal of Membrane Science 135:99-106.
Chen et al. 2006. A noninterference polypyrrole glucose biosensor. Biosensors and Bioelectronics 22:639-643.
Ciba® Irgacure® 2959 Photoinitiator, Product Description. Apr. 2, 1998. Ciba Specialty Chemicals Inc., Basel, Switzerland. 3 pages.
Claremont et al. 1986. Subcutaneous implantation of a ferrocene-mediated glucose sensor in pigs. Diabetologia 29:817-821.
Claremont et al. Jul. 1986. Potentially-implantable, ferrocene-mediated glucose sensor. J. Biomed. Eng. 8:272-274.
Clark et al. 1981. One-minute electrochemical enzymic assay for cholesterol in biological materials, Clin. Chem. 27(12):1978-1982.
Clark et al. 1987. Configurational cyclic voltammetry: increasing the specificity and reliablity of implanted electrodes, IEEE/Ninth Annual Conference of the Engineering in Medicine and Biology Society, pp. 0782-0783.
Clark et al. 1988. Long-term stability of electroenzymatic glucose sensors implanted in mice. Trans Am Soc Artif Intern Organs 34:259-265.
Clarke et al. (Jan. 1987). Evaluating Clinical Accuracy of Systems for Self-Monitoring of Blood Glucose. Diabetes Care 10(5):622-628.
CLSI. Performance metrics for continuous interstitial glucose monitoring; approved guideline, CLSI document POCT05-A. Wayne, PA: Clinical and Laboratory Standards Institute: 2008 28(33), 72 pp.
Colangelo et al. 1967. Corrosion rate measurements in vivo, Journal of Biomedical Materials Research, 1:405-414.
Colowick et al. 1976. Methods in Enzymlology, vol. XLIV, Immobilized Enzymes. New York: Academic Press.
Cox et al. 1985. Accuracy of perceiving blood glucose in IDDM. Diabetes Care 8(6):529-536.
Csoregi et al., 1994. Design, characterization, and one-point in vivo calibration of a subcutaneously implanted glucose electrode. Anal Chem. 66(19):3131-3138.
Dai et al. 1999. Hydrogel Membranes with Mesh Size Asymmetry Based on the Gradient Crosslink of Poly(vinyl alcohol). Journal of Membrane Science 156:67-79.
Danielsson et al. 1988. Enzyme thermistors, Methods in Enzymology, 137:181-197.
D'Arrigo et al. 2003. Porous-Si based bioreactors for glucose monitoring and drugs production. Proc. of SPIE 4982: 178-184.
Dassau et al., In silico evaluation platform for artifical pancreatic β-cell development—a dynamic simulator for closed loop control with hardware-in-the-loop, Diabetes Technology & Therapeutics, 11(3):1-8, 2009.
Davies, et al. 1992. Polymer membranes in clinical sensor applications. I. An overview of membrane function, Biomaterials, 13(14):971-978.
Direct 30/30® Blood Glucose Sensor, (Markwell Medical) Catalog, ©1990, ELCO Diagnostics Company. 1 page.
Dixon et al. 2002. Characterization in vitro and in vivo of the oxygen dependence of an enzyme/polymer biosensor for monitoring brain glucose. Journal of Neuroscience Methods 119:135-142.
DuPont[1] Dimension AR®. 1998. The chemistry analyzer that makes the most of your time, money and effort. Catalog. Dade International, Chemistry Systems. Newark, DE. 18 pages.
El Degheidy et al. 1986. Optimization of an implantable coated wire glucose sensor. J. Biomed Eng. 8: 121-129.
Electronic File History of U.S. Appl. No. 09/447,227, filed Nov. 22, 1999 containing Office Actions dated Aug. 15, 2000; Jan. 17, 2002; Jul. 15, 2002; Sep. 25, 2002; Jan. 10, 2003; Jul. 9, 2003; Nov. 23, 2003; Feb. 5, 2004; Sep. 22, 2005; Apr. 4, 2006; Jun. 27, 2006; Aug. 1, 2006; Mar. 9, 2007; Jul. 17, 2007; Jan. 23, 2008; Jun. 12, 2008; Dec. 11, 2008; May 26, 2009; Dec. 8, 2009; Jan. 14, 2010; May 18, 2010, and Oct. 14, 2010 and Applicant Responses filed May 24, 2002; Sep. 16, 2002; Nov. 19, 2002; Apr. 18, 2003; Aug. 5, 2003; Nov. 5, 2003; Jan. 15, 2004; Dec. 27, 2005; Jun. 8, 2006; Jul. 20, 2006; Dec. 4, 2006; May 2, 2007; Sep. 14, 2007; Nov. 5, 2007; Mar. 21, 2008; Sep. 5, 2008; Mar. 9, 2009; Aug. 24, 2009; Oct. 1, 2009; Dec. 22, 2009; Feb. 25, 2010 and May 28, 2010.
Electronic File History of ex parte Reexamination Control No. 90/011,345, filed Nov. 19, 2010 containing Office Action(s) dated Dec. 16, 2010, Jan. 12, 2011 and Apr. 26, 2011, and Applicant(s) Response filed Mar. 14, 2011.
Electronic File History of ex parte Reexamination Control No. 90/011,466, filed Jan. 31, 2011 containing Office Action(s) dated Feb. 10, 2011, Feb. 25, 2011 and Apr. 18, 2011, and Applicant(s) Response filed Jun. 20, 2011 as of Aug. 25, 2011.
Electronic File History of ex parte Reexamination Control No. 90/011,683, filed May 10, 2011 containing Office Action(s) dated May 20, 2011, May 24, 2011 and Jun. 14, 2011, and Applicant(s) Response filed Aug. 15, 2011 as of Aug. 25, 2011.
Electronic File History of ex parte Reexamination Control No. 90/011,722, filed May 31, 2011 containing Office Action(s) dated Jul. 28, 2011 as of Aug. 25, 2011.
Electronic File History of ex parte Reexamination Control No. 90/011,776, filed Jun. 29, 2011 containing Office Action(s) dated Jul. 11, 2011 and Aug. 15, 2011 as of Aug. 25, 2011.
Electronic File History of ex parte Reexamination Control No. 90/011,814, filed Jul. 28, 2011 containing Office Action(s) dated Aug. 3, 2011 as of Aug. 25, 2011.
Electronic File History of U.S. Appl. No. 09/916,858, filed Jul. 27, 2001 (USP 6,862,465, issued Mar. 1, 2005) containing Office Actions dated Mar. 22, 2004; Sep. 24, 2004, and Nov. 15, 2004 and Applicant Responses filed Jun. 24, 2004 and Oct. 12, 2004.
Electronic File History of U.S. Appl. No. 10/657,843, filed Sep. 9, 2003 (USP 7,110,803, issued Sep. 19, 2006), containing Office Actions dated Sep. 21, 2004; Jan. 10, 2005 and Applicant Responses filed Oct. 12, 2004; Feb. 2, 2005; May 23, 2005 and Mar. 13, 2006.
Electronic File History of U.S. Appl. No. 10/846,150, filed May 14, 2004 (abandoned), containing Office Actions dated Feb. 21, 2008; Jun. 5, 2008; Dec. 9, 2008; Jun. 9, 2009; Jan. 7, 2010, and Jun. 4, 2010 and Applicant Responses filed Oct. 25, 2007; Feb. 26, 2008; Sep. 5, 2008; Mar. 5, 2009; Oct. 9, 2009; Mar. 1, 2010.
Electronic File History of U.S. Appl. No. 11/021,046, filed Dec. 22, 2004 (USP 7,711,402, issued May 4, 2010) containing Office Actions dated Dec. 26, 2007; Jun. 23, 2008; Feb. 4, 2009; Aug. 19, 2009; Dec. 1, 2009, and Apr. 5, 2010 and Applicant Responses filed Feb. 27, 2008; Nov. 14, 2008; May 4, 2009; Oct. 21, 2009, and Dec. 15, 2009.
Electronic File History of U.S. Appl. No. 11/039,269, filed Jan. 19, 2005 (USP 7,136,689, issued Nov. 14, 2006) containing Office Actions dated May 4, 2005; Nov. 2, 2005; Feb. 24, 2006; Aug. 14, 2006, and Sep. 6, 2006 and Applicant Responses filed Aug. 18, 2005; Feb. 6, 2006; May 26, 2006; Aug. 17, 2006; Aug. 23, 2006.
Electronic File History of U.S. Appl. No. 11/546,157, filed Oct. 10, 2006 (abandoned) containing Office Action dated Jan. 14, 2010 and Feb. 26, 2010 and Applicant Response filed Jan. 28, 2010.
Electronic File History of U.S. Appl. No. 12/037,812, filed Feb. 26, 2008 (now USP 7,860,545, issued Dec. 28, 2010) containing Office Actions dated Sep. 29, 2008; Apr. 1, 2009; Jul. 24, 2009; Jun. 4, 2010, and Sep. 28, 2010 and Applicant Responses dated Dec. 9, 2008; May 15, 2009; Oct. 26, 2009; Sep. 2, 2010.
Electronic File History of U.S. Appl. No. 12/037,830, filed Feb. 26, 2008 (abandoned) containing Office Actions dated Sep. 29, 2008; Feb. 26, 2009; Jun. 1, 2009; Aug. 7, 2009; Feb. 23, 2010, and Jun. 11, 2010 and Applicant Responses dated Dec. 9, 2008; May 7, 2009; Jun. 3, 2009; Nov. 5, 2009; Mar. 2, 2010.
Electronic File History of U.S. Appl. No. 12/645,097, filed Dec. 22, 2009 (now USP 7,792,561, issued Sep. 7, 2010) containing Office Actions dated Jun. 28, 2010 and Applicant Preliminary Amendments filed Dec. 22, 2009; Mar. 1, 2010, and May 14, 2010.
Electronic File History of U.S. Appl. No. 12/645,270, filed Dec. 22, 2009 (now USP 7,835,777, issued Nov. 16, 2010) containing Office Actions dated May 12, 2010 and Sep. 22, 2010 and Applicant Response filed Jun. 2, 2010.

(56) References Cited

OTHER PUBLICATIONS

Electronic File History of U.S. Appl. No. 12/763,013, filed Apr. 19, 2010 (now USP 7,974,672, issued Jul. 5, 2011 containing Office Actions dated Sep. 15, 2010 and Applicant Response dated Dec. 15, 2010.
Electronic File History of U.S. Appl. No. 12/763,016, filed Apr. 19, 2010 (now USP 7,970,448, issued Jun. 28, 2011) containing Office Actions dated Sep. 15, 2010 and Applicant Response dated Dec. 15, 2010.
English translation of Office Action received Dec. 19, 2007 in Japanese App. No. 10/538680.
Ernst et al. 2002. Reliable glucose monitoring through the use of microsystem technology. Anal. Bioanal. Chem. 373:758-761.
European Search Report for App. No. 98908875.2 dated Apr. 29, 2004.
Fare et al. 1998. Functional characterization of a conducting polymer-based immunoassay system. Biosensors & Bioelectronics 13(3-4):459-470.
Feldman et al. 2003. A continuous glucose sensor based on wired enzyme technology—results from a 3-day trial in patients with type 1 diabetes. Diabetes Technol Ther 5(5):769-779.
Fischer et al. 1987. Assessment of subcutaneous glucose concentration: validation of the wick technique as a reference for implanted electrochemical sensors in normal and diabetic dogs, Diabetologia 30:940-945.
Fischer et al. 1989. Oxygen Tension at the Subcutaneous Implantation Site of Glucose Sensors. Biomed. Biochem 11/12:965-972.
Freedman et al. 1991. Statistics, Second Edition, W.W. Norton & Company, p. 74.
Frohnauer et al. 2001. Graphical human insulin time-activity profiles using standardized definitions. Diabetes Technology & Therapeutics 3(3):419-429.
Frost et al. 2002. Implantable chemical sensors for real-time clinical monitoring: Progress and challenges. Current Opinion in Chemical Biology 6:633-641.
Gabbay et al. 2008. Optical coherence tomography-based continuous noninvasive glucose monitoring in patients with diabetes. Diab. Thechnol. & Therapeut., 10:188-193.
Ganesan et al., 2005, Gold layer-based dual crosslinking procedure of glucose oxidase with ferrocene monocarboxylic acid provides a stable biosensor, Analytical Biochemistry 343:188-191.
Ganesh et al. Mar. 2008. Evaluation of the VIA® blood chemistry monitor for glucose in healthy and diabetic volunteers, Journal of Diabetes Science and Technology, 2(2): 182-193.
Gao et al. 1989. Determination of Interfacial parameters of cellulose acetate membrane materials by HPLC, J. Liquid Chromatography, VI. 12, n. 11, 2083-2092.
Garg et al. 2004. Improved Glucose Excursions Using an Implantable Real-Time continuous Glucose Sensor in Adults with Type I Diabetes. Diabetes Care 27:734-738.
Geller et al. 1997. Use of an immunoisolation device for cell transplantation and tumor immunotherapy. Ann NY Acad Sci 831:438-451.
Gerritsen et al. 1999. Performance of subcutaneously implanted glucose sensors for continuous monitoring. The Netherlands Journal of Medicine 54:167-179.
Gerritsen, et al. 2001. Influence of inflammatory cells and serum on the performance of implantable glucose sensors. J Biomed Mater Res 54:69-75.
Gerritsen, M. 2000. Problems associated with subcutaneously implanted glucose sensors. Diabetes Care 23(2):143-145.
Gilligan et al. 1994. Evaluation of a subcutaneous glucose sensor out to 3 months in a dog model. Diabetes Care 17(8):882-887.
Gilligan et al. 2004, Feasibility of continuous long-term glucose monitoring from a subcutaneous glucose sensor in humans. Diabetes Technol Ther 6:378-386.
Godsland et al. 2001. Maximizing the Success Rate of Minimal Model Insulin Sensitivity Measurement in Humans: The Importance of Basal Glucose Levels. The Biochemical Society and the Medical Research Society, 1-9.

Gouda et al., Jul. 4, 2003. Thermal inactiviation of glucose oxidase, The Journal of Biological Chemistry, 278(27):24324-24333.
Gough et al. 2000. Immobilized glucose oxidase in implantable glucose sensor technology. Diabetes Technology & Therapeutics 2(3):377-380.
Gough et al. 2003. Frequency characterization of blood glucose dynamics. Annals of Biomedical Engineering 31:91-97.
Gregg et al. 1990. Cross-Linked Redox Gels Containing Glucose Oxidase for Amperometric Biosensor Applications. Anal. Chem. 62:258-263.
Gross et al. 2000. Efficacy and reliability of the continuous glucose monitoring system. Diabetes Technology & Therapeutics, 2(Suppl 1):S19-26.
Gross et al. 2000. Performance evaluation of the MiniMed® continuous glucose monitoring system during patient home use. Diabetes Technology & Therapeutics 2(1):49-56.
Guerci et al., Clinical performance of CGMS in type 1 diabetic patents treated by continuous subcutaneous insulin infusion using insulin analogs, Diabetes Care, 26:582-589, 2003.
Guo et al 1998. Modification of cellulose acetate ultrafiltration membrane by gamma ray radiation, Shuichuli Jishi Bianji Weiyuanhui, 23(6):315-318 (Abstract only).
Hall et al. 1998. Electrochemical oxidation of hydrogen peroxide at platinum electrodes. Part I: An adsorption-controlled mechanism. Electrochimica Acta, 43(5-6):579-588.
Hall et al. 1998. Electrochemical oxidation of hydrogen peroxide at platinum electrodes. Part II: Effect of potential. Electrochimica Acta 43(14-15):2015-2024.
Hall et al. 1999. Electrochemical oxidation of hydrogen peroxide at platinum electrodes. Part III: Effect of temperature. Electrochimica Acta, 44:2455-2462.
Hall et al. 1999. Electrochemical oxidation of hydrogen peroxide at platinum electrodes. Part IV: Phosphate buffer dependence. Electrochimica Acta, 44:4573-4582.
Hall et al. 2000. Electrochemical oxidation of hydrogen peroxide at platinum electrodes. Part V: Inhibition by chloride. Electrochimica Acta, 45:3573-3579.
Hamilton Syringe Selection Guide. 2006. Syringe Selection. www.hamiltoncompany.com.
Harrison et al. 1988. Characterization of perfluorosulfonic acid polymer coated enzyme electrodes and a miniaturized integrated potentiostat for glucose analysis in whole blood. Anal. Chem. 60:2002-2007.
Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," Diabetes Care, 17(5): 387-396.
Heller, "Electrical wiring of redox enzymes," Acc. Chem. Res., 23:128-134 (1990).
Heller, A. 1992. Electrical Connection of Enzyme Redox Centers to Electrodes. J. Phys. Chem. 96:3579-3587.
Heller, A. 1999. Implanted electrochemical glucose sensors for the management of diabetes. Annu Annu Rev Biomed Eng 1:153-175.
Heller, A. 2003. Plugging metal connectors into enzymes. Nat Biotechnol 21:631-2.
Hicks, 1985. In Situ Monitoring, Clinical Chemistry, 31(12):1931-1935.
Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.
Hoel, Paul G. 1976. Elementary Statistics, Fourth Edition. John Wiley & Sons, Inc.. pp. 113-114.
Hrapovic et al. 2003. Picoamperometric detection of glucose at ultrasmall platinum-based biosensors: preparation and characterization. Anal Chem 75:3308-3315.
http://www.merriam-webster.com/dictionary, definition for "aberrant," Aug. 19, 2008, p. 1.
Hu, et al. 1993. A needle-type enzyme-based lactate sensor for in vivo monitoring, Analytica Chimica Acta, 281:503-511.

(56) References Cited

OTHER PUBLICATIONS

Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode. U.S. Department of Commerce/NTIS, pp. 1-116.

Huang et al., Sep. 1997, A 0.5mW Passive Telemetry IC for Biomedical Applications, Proceedings of the 23rd European Solid-State Circuits Conference (ESSCIRC '97), pp. 172-175, Southampton, UK.

Hunter et al. Mar. 31, 2000. Minimally Invasive Glucose Sensor and Insulin Delivery System. MIT Home Automation and Healthcare Consortium. Progress Report No. 2-5. 17 pages.

International Preliminary Examination Report dated Jun. 4, 2003 in PCT/US2001/23850, filed Jul. 30, 2001.

International Search Report dated Jan. 16, 2002 in PCT/US2001/23850, filed Jul. 30, 2001.

International Search Report dated Jul. 9, 1998 in PCT/US1998/04090, filed Mar. 3, 1998.

Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Complications, 12:295-301.

Jaffari et al., Recent advances in amperometric glucose biosensors for in vivo monitoring, Physiol. Meas. 16 (1995) 1-15.

Jensen et al. 1997. Fast wave forms for pulsed electrochemical detection of glucose by incorporation of reductive desorption of oxidation products. Analytical Chemistry 69(9):1776-1781.

Jeutter, D. C. 1982. A transcutaneous implanted battery recharging and biotelemeter power switching system. IEEE Trans Biomed Eng 29:314-321.

Jobst et al., Thin-Film Microbiosensors for Glucose-Lactate Monitoring, Anal Chem. (1996) 68(18): 3173-3179.

Johnson et al. 1992. In vivo evaluation of an electroenzymatic glucose sensor implanted in subcutaneous tissue. Biosensors & Bioelectronics, 7:709-714.

Johnson, R.C. et al. 1997. Abstract: Neovascularization of cell transplantation devices: Role of membrane architecture and encapsulated tissue, Abstracts of Papers, Am. Chem. Soc., 214:2 p. 305-PMSE.

Jovanovic, L. 2000. The role of continuous glucose monitoring in gestational diabetes mellitus. Diabetes Technology & Therapeutics, 2 Suppl 1, S67-71.

Kamath et al. Calibration of a continuous glucose monitor: effect of glucose rate of change, Eighth Annual Diabetes Technology Meeting, Nov. 13-15, 2008, p. A88.

Karube et al. 1993. Microbiosensors for acetylcholine and glucose. Biosensors & Bioelectronics 8:219-228.

Kaufman et al. 2001. A pilot study of the continuous glucose monitoring system. Diabetes Care 24(12):2030-2034.

Kaufman. 2000. Role of the continuous glucose monitoring system in pediatric patients. Diabetes Technology & Therapeutics 2(1):S-49-S-52.

Kawagoe et al. 1991. Enzyme-modified organic conducting salt microelectrode, Anal. Chem. 63:2961-2965.

Keedy et al. 1991. Determination of urate in undiluted whole blood by enzyme electrode. Biosensors & Bioelectronics, 6: 491-499.

Kerner et al. 1988. A potentially implantable enzyme electrode for amperometric measurement of glucose, Horm Metab Res Suppl. 20:8-13.

Kerner et al. 1993. "The function of a hydrogen peroxide-detecting electroenzymatic glucose electrode is markedly impaired in human sub-cutaneous tissue and plasma," Biosensors & Bioelectronics, 8:473-482.

Kiechle, F.L. 2001. The impact of continuous glucose monitoring on hospital point-of-care testing programs. Diabetes Technol Ther 3:647-649.

Klueh et al. 2003. Use of Vascular Endothelial Cell Growth Factor Gene Transfer to Enhance Implantable Sensor Function in Vivo, Biosensor Function and Vegf-Gene Transfer, pp. 1072-1086.

Klueh et al. 2007. Inflammation and glucose sensors: use of dexamethasone to extend glucose sensor function and life span in vivo. Journal of Diabetes Science and Technology 1(4):496-504.

Kondo et al. 1982. A miniature glucose sensor, implantable in the blood stream. Diabetes Care. 5(3):218-221.

Koschinsky et al. 1988. New approach to technical and clinical evaluation of devices for self-monitoring of blood glucose. Diabetes Care 11(8): 619-619.

Koschinsky et al. 2001. Sensors for glucose monitoring: Technical and clinical aspects. Diabetes Metab. Res. Rev. 17:113-123.

Kost et al. 1985. Glucose-sensitive membranes containing glucose oxidase: activitiy, swelling, and permeability studies, Journal of Biomedical Materials Research 19:1117-1133.

Koudelka et al. 1989. In vivo response of microfabricated glucose sensors to glycemia changes in normal rats. Biomed Biochim Acta 48(11-12):953-956.

Koudelka et al. 1991. In-vivo behaviour of hypodermically implanted microfabricated glucose sensors. Biosensors & Bioelectronics 6:31-36.

Kraver et al. 2001. A mixed-signal sensor interface microinstrument. Sensors and Actuators A 91:266-277.

Kruger et al. 2000. Psychological motivation and patient education: A role for continuous glucose monitoring. Diabetes Technology & Therapeutics, 2(Suppl 1):S93-97.

Kulys et al., 1994. Carbon-paste biosensors array for long-term glucose measurement, Biosensors& Beioelectronics, 9:491-500.

Kunjan et al. Mar. 2008. Automated blood sampling and glucose sensing in critical care settings, Journal of Diabetes Science and Technology 2(3):194-200.

Kunzler et al. 1993. Hydrogels based on hydrophilic side chain siloxanes. Poly Mat Sci and Eng 69:226-227.

Kunzler et al. Aug. 21, 1995. Contact lens materials. Chemistry & Industry. 651-655.

Kusano, H. Glucose enzyme electrode with percutaneous interface which operates independently of dissolved oxygen. Clin Phys Physiol Meas. 1989. 10(1): 1-9.

Lee et al. 1999. Effects of pore size, void volume, and pore connectivity on tissue responses. Society for Biomaterials 25th Annual Meeting, 171.

Lehmann et al. May 1994. Retrospective valication of a physiological model of glucoseiunsulin interaaction in tyhpe 1 diabetes mellitus, Med. Eng. Phys. 16:193-202.

Lerner et al. 1984. An implantable electrochemical glucose sensor. Ann. N. Y. Acad. Sci. 428:263-278.

Lewandowski et al. 1988. Evaluation of a miniature blood glucose sensor. Trans Am Soc Artif Intern Organs 34:255-258.

Leypoldt et al. 1984. Model of a two-substrate enzyme electrode for glucose. Anal. Chem. 56:2896-2904.

Linke et al. 1994. Amperometric biosensor for in vivo glucose sensing based on glucose oxidase immobilized in a redox hydrogel. Biosensors & Bioelectronics 9:151-158.

Loffler et al. 1995. Separation and determination of traces of ammonia in air by means of chromatomembrane cells. Fresenius J Anal Chem 352:613-614.

Lowe, 1984. Biosensors, Trends in Biotechnology, 2(3):59-65.

Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.

Lyandres et al. (2008). Progress toward an in vivo surface-enhanced raman spectroscopy glucose sensor. Diabetes Technology & Therapeutics, 10(4): 257-265.

Lyman D. 1960. Polyurethanes. I. The Solution Polymerization of Diisocyanates with Ethylene Glycol. J. Polymer Sci XLV:45:49.

Madaras et al. 1996. Microfabricated amperometric creatine and creatinine biosensors. Analytica Chimica Acta 319:335-345.

Maidan et al. 1992. Elimination of Electrooxidizable Interferent-Produced Currents in Amperometric Biosensors, Analytical Chemistry, 64:2889-2896.

Makale et al. 2003. Tissue window chamber system for validation of implanted oxygen sensors. Am. J. Physiol. Heart Circ. Physiol. 284:H2288-2294.

(56) References Cited

OTHER PUBLICATIONS

Malin et al. 1999. Noninvasive Prediction of Glucose by Near-Infrared Diffuse Reflectance Spectroscopy. Clinical Chemistry 45:9, 1651-1658.

Maran et al. 2002. Continuous subcutaneous glucose monitoring in diabetic patients: A multicenter analysis. Diabetes Care 25(2):347-352.

March, W. F. 2002. Dealing with the delay. Diabetes Technol Ther 4(1):49-50.

Mastrototaro et al. 1991 "An electroenzymatic glucose sensor fabricated on a flexible substrate," Sensors and Actuators B, 5:139-44.

Mastrototaro, J. J. 2000. The MiniMed continuous glucose monitoring system. Diabetes Technol Ther 2(Suppl 1):S13-8.

Mastrototaro et al. 2003. Reproducibility of the continuous glucose monitoring system matches previous reports and the intended use of the product. Diabetes Care 26:256; author reply p. 257.

Matsumoto et al. 1998. A micro-planar amperometeric glucose sensor unsusceptible to interference species. Sensors and Actuators B 49:68-72.

Matsumoto et al. 2001. A long-term lifetime amperometric glucose sensor with a perfluorocarbon polymer coating. Biosens Bioelectron 16:271-276.

Mazze et al. 2008. Characterizing glucose exposure for individuals with normal glucose tolerance using continuous glucose monitoring and ambulatory glucose profile analysis. Diab. Thechnol. & Therapeut., 10:149-159.

McCartney et al. 2001. Near-infrared fluorescence lifetime assay for serum glucose based on allophycocyanin-labeled concanavalin A. Anal Biochem 292:216-221.

McKean et al. Jul. 7, 1988. A Telemetry Instrumentation System for Chronically Implanted Glucose and Oxygen Sensors. Transactions on Biomedical Engineering 35:526-532.

Memoli et al. 2002. A comparison between different immobilised glucoseoxidase-based electrodes. J Pharm Biomed Anal 29:1045-1052.

Merriam-Webster Online Dictionary. Jan. 11, 2010. Definition of "acceleration". http://www.merriam-webster.com/dictionary/Acceleration.

Merriam-Webster Online Dictionary. Jan. 11, 2010. Definition of "system". http://www.merriam-webster.com/dictionary/System.

Merriam-Webster Online Dictionary. Apr. 23, 2007. Definition of "nominal". http://www.merriam-webster.com/dictionary/nominal.

Meyerhoff et al. 1992. On line continuous monitoring of subcutaneous tissue glucose in men by combining portable glucosensor with microdialysis. Diabetologia 35(11):1087-1092.

Moatti-Sirat et al. 1992. Evaluating in vitro and in vivo the interference of ascorbate and acetaminophen on glucose detection by a needle-type glucose sensor, Biosensors & Bioelectronics 7:345-352.

Moatti-Sirat et al. 1992. Towards continuous glucose monitoring: in vivo evaluation of a miniaturized glucose sensor implanted for several days in rat subcutaneous tissue. Diabetologia 35:224-230.

Moatti-Sirat et al. Jun. 1994. Reduction of acetaminophen interference in glucose sensors by a composite Nafion membrane: demonstration in rats and man, Diabetologia 37(6):610-616.

Morff et al. 1990. Microfabrication of reproducible, economical, electroenzymatic glucose sensors, Annual International Conference of the IEEE Engineering in Medicine and Biology Society, 12(2):0483-0484.

Mosbach et al. 1975. Determination of heat changes in the proximity of immobilized enzymes with an enzyme termistor and its use for the assay of metobolites, Biochim. Biophys. Acta. (Enzymology), 403:256-265.

Motonaka et al. 1993. Determination of cholesteral and cholesteral ester with novel enzyme microsensors, Anal. Chem. 65:3258-3261.

Moussy et al. 2000. Biomaterials community examines biosensor biocompatibility Diabetes Technol Ther 2:473-477.

Moussy et al. 1993. Performance of subcutaneously implanted needle-type glucose sensors employing a novel trilayer coating, Anal Chem. 85: 2072-2077.

Moussy, Francis (Nov. 2002) Implantable Glucose Sensor: Progress and Problems, Sensors, 1:270-273.

Mowery et al. 2000. Preparation and characterization of hydrophobic polymeric films that are thromboresistant via nitric oxide release. Biomaterials 21:9-21.

Murphy, et al. 1992. Polymer membranes in clinical sensor applications. II. The design and fabrication of permselective hydrogels for electrochemical devices, Biomaterials, 13(14):979-990.

Myler et al. 2002. Ultra-thin-polysiloxane-film-composite membranes for the optimisation of amperometric oxidase enzyme electrodes. Biosens Bioelectron 17:35-43.

Nafion® 117 Solution Product Description, Product No. 70160, Sigma-Aldrich Corp., St. Louis, MO. Downloaded from https://www.signaaldrich.com/cgi-bin/hsrun/Suite7/Suite/HAHTpage/Suite.HsExternal Prod . . . on Apr. 7, 2005.

Nam et al. 2000. A novel fabrication method of macroporous biodegradable polymer scaffolds using gas foaming salt as a porogen additive. J Biomed Mater Res 53:1-7.

Ohara et al. 1994. "Wired" enzyme electrodes for amperometric determination of glucose or lactate in the presence of interfering substances. Anal Chem 66:2451-2457.

Ohara, et al. Dec. 1993. Glucose electrodes based on cross-linked bis(2,2'- bipyridine)chloroosmium(+/2+) complexed poly(1-vinylimidazole) films, Analytical Chemistry, 65:3512-3517.

Okuda et al. 1971. Mutarotase effect on micro determinations of D-glucose and its anomers with β-D-glucose oxidase. Anal Biochem 43:312-315.

Oxford English Dictionary Online. Definition of "impending". http://www.askoxford.com/results/?view=dev dict&field-12668446 Impending&branch= Jan. 11, 2010.

Palmisano et al. 2000. Simultaneous monitoring of glucose and lactate by an interference and cross-talk free dual electrode amperometric biosensor based on electropolymerized thin films. Biosensors & Bioelectronics 15:531-539.

Panetti 2002. Differential effects of sphingosine 1-phosphate and lysophosphatidic acid on endothelial cells. Biochimica et Biophysica Acta 1582:190-196.

Park et al. 2002. Gas separation properties of polysiloxane/polyether mixed soft segment urethane urea membranes, J. Membrane Science, 204: 257-269.

Patel et al. 2003. Amperometric glucose sensors based on ferrocene containing polymeric electron transfer systems—a preliminary report. Biosens Bioelectron 18:1073-6.

Peacock et al. 2008. Cardiac troponin and outcome in acute heart failure. N. Engl. J. Med., 358: 2117-2126.

Pegoraro et al. 1995. Gas transport properties of siloxane polyurethanes, Journal of Applied Polymer Science, 57:421-429.

Pfeiffer et al. 1992. On line continuous monitoring of subcutaneous tissue glucose is feasible by combining portable glucosensor with microdialysis. Horm. Metab. Res. 25:121-124.

Pfeiffer, E.F. 1990. The glucose sensor: the missing link in diabetes therapy, Horm Metab Res Suppl. 24:154-164.

Phillips and Smith. 1988. Bromedical Applications of Polyurethanes: Implications of Failure Mechanisms. J. Biomat. Appl. 3:202-227.

Pichert et al. 2000. Issues for the coming age of continuous glucose monitoring Diabetes Educ 26(6):969-980.

Pickup et al. "Implantable glucose sensors: choosing the appropriate sensing strategy," Biosensors, 3:335-346 (1987/88).

Pickup et al. 1988. Progress towards in vivo glucose sensing with a ferrocene-mediated amperometric enzyme electrode. 34-36.

Pickup et al. "In vivo molecular sensing in diabetes mellitus: an implantable glucose sensor with direct electron transfer," Diabetologia, 32:213-217 (1989).

Pickup et al. 1989. Potentially-implantable, amperometric glucose sensors with mediated electron transfer: improving the operating stability. Biosensors 4:109-119.

Pineda et al. 1996. Bone regeneration with resorbable polymeric membranes. III. Effect of poly(L-lactide) membrane pore size on the bone healing process in large defects. J. Biomedical Materials Research 31:385-394.

Pinner et al. Oct. 1959. Cross-linking of cellulose acetate by ionizing radiation, Nature, 184: 1303-1304.

(56) References Cited

OTHER PUBLICATIONS

Pishko et al. 1991. "Amperometric glucose microelectrodes prepared through immobilization of glucose oxidase in redox hydrogels," Anal. Chem., 63:2268-72.
Pitzer et al. 2001. Detection of hypoglycemia with the GlucoWatch biographer. Diabetes Care 24(5):881-885.
Poitout et al. 1991. In Vitro and In Vivo Evaluation in Dogs of a Miniaturized Glucose Sensor, ASAIO Transactions, 37:M298-M300.
Poitout et al. 1993. A glucose monitoring system for on line estimation in man of blood glucose concentration using a miniaturized glucose sensor implanted in the subcutaneous tissue and a wearable control unit. Diabetologia 36:658-663.
Poitout et al. 1994. Development of a glucose sensor for glucose monitoring in man: the disposable implant concept. Clinical Materials 15:241-246.
Postlethwaite et al. 1996. Interdigitated array electrode as an alternative to the rotated ring-disk electrode for determination of the reaction products of dioxygen reduction. Analytical Chemistry 68:2951-2958.
Prabhu et al. 1981. Electrochemical studies of hydrogen peroxide at a platinum disc electrode, Electrochimica Acta 26(6):725-729.
Quinn et al. 1995. Kinetics of glucose delivery to subcutaneous tissue in rats measured with 0.3-mm amperometric microsensors. The American Physiological Society E155-E161.
Quinn et al. 1997. Biocompatible, glucose-permeable hydrogel for in situ coating of implantable biosensors. Biomaterials 18:1665-1670.
Rabah et al., 1991. Electrochemical wear of graphite anodes during electrolysis of brine, Carbon, 29(2):165-171.
Ratner, B.D. 2002. Reducing capsular thickness and enhancing angiogenesis around implant drug release systems. J Control Release 78:211-218.
Reach et al. 1986. A Method for Evaluating in vivo the Functional Characteristics of Glucose Sensors. Biosensors 2:211-220.
Reach et al. 1992. Can continuous glucose monitoring be used for the treatment of diabetes? Analytical Chemistry 64(5):381-386.
Reach et al., (Mar. 1993) Continuous glucose sensing for the treatment of diabetes mellitus, Analusis Magazine, 21(2): M35-M39.
Reach, G. 2001. Which threshold to detect hypoglycemia? Value of receiver-operator curve analysis to find a compromise between sensitivity and specificity. Diabetes Care 24(5):803-804.
Rebrin et al. "Automated feedback control of subcutaneous glucose concentration in diabetic dogs," Diabetologia, 32:573-76 (1989).
Rebrin et al. 1992. Subcutaneous glucose monitoring by means of electrochemical sensors: fiction or reality? J. Biomed. Eng. 14:33-40.
Request for Ex Parte Reexamination Control No. 90/011,722 dated Sep. 14, 2012 for U.S. Appl. No. 12/645,270, filed Dec. 22, 2009 (USP 7,835,777); TOC, 3 pgs.
Request for Ex Parte Reexamination Control No. 90/011,884 dated Aug. 30, 2011 for U.S. Appl. No. 12/763,016, filed Apr. 19, 2010 (USP 7,970,488); TOC, 3 pgs.
Request for Ex Parte Reexamination Control No. 90/011,905 dated Sep. 14, 2011 for U.S. Appl. No. 12/763,013, filed Apr. 19, 2010 (USP 7,974,672); TOC, 3 pgs.
Request for Ex Parte Reexamination Control No. 90/011,610, filed Mar. 31, 2011 U.S. Patent No. 7,899,511, issued Mar. 1, 2011; TOC, pp. 3.
Request for Ex Parte Reexamination Control No. 90/011,468, filed Feb. 1, 2011 of U.S. Patent No. 7,771,352, Issued Oct. 4, 2011; TOC, pp. 3.
Reusch. 2004. Chemical Reactivity. Organometallic Compounds. Virtual Textbook of Organic Chem. pp. 1-16, http://www.cem.msu.edu/~reusch/VirtualText/orgmetal.htm.
Rhodes et al. 1994. Prediction of pocket-portable and implantable glucose enzyme electrode performance from combined species permeability and digital simulation analysis. Analytical Chemistry 66(9):1520-1529.
Rigla et al. 2008. Real-time continuous glucose monitoring together with telemedical assistance improves glycemic control and glucose stability in pump-treated patients. Diab. Technol. & Therapeut., 10(3): 194-199.
Rivers et al. 2001. Central venous oxygen saturation monitoring in the critically ill patient, Current Opinion in Critical Care, 7:204-211.
Sachlos et al. 2003. Making Tissue Engineering Scaffolds Work. Review on the Application of Sold Freeform Fabrication Technology to the Production of Tissue Engineering Scaffolds. European Cells and Materials 5:29-40.
Sakakida et al. 1992. Development of Ferrocene-Mediated Needle-Type Glucose Sensor as a Measure of True Subcutaneous Tissue Glucose Concentrations. Artif. Organs Today 2(2):145-158.
Sakakida et al. 1993. Ferrocene-Mediated Needle Type Glucose Sensor Covered with Newly Designed Biocompatible Membran, Sensors and Actuators B 13-14:319-322.
Salardi et al. 2002. The glucose area under the profiles obtained with continuous glucose monitoring system relationships with HbA1c in pediatric type 1 diabetic patients. Diabetes Care 25(10):1840-1844.
Samuels, M.P. 2004. The effects of flight and altitude. Arch Dis Child. 89: 448-455.
Sansen et al. 1985. "Glucose sensor with telemetry system." in Ko, W. H. (Ed.). Implantable Sensors for Closed Loop Prosthetic Systems. Chap. 12, pp. 167-175, Mount Kisco, NY: Futura Publishing Co.
Sansen et al. 1990. A smart sensor for the voltammetric measurement of oxygen or glucose concentrations. Sensors and Actuators B 1:298-302.
Schmidt et al. 1993. Glucose concentration in subcutaneous extracellular space. Diabetes Care 16(5):695-700.
Schmidtke et al. Jan. 1998. Measurement and modeling of the transient difference between blood and subcutaneous glucose concentrations in the rat after injection of insulin. Proc Natl Acad Sci U S A, 95: 294-299.
Schoemaker et al. 2003. The SCGM1 system: Subcutaneous continuous glucose monitoring based on microdialysis technique. Diabetes Technology & Therapeutics 5(4):599-608.
Schoonen et al. 1990. Development of a potentially wearable glucose sensor for patients with diabetes mellitus: design and in-vitro evaluation. Biosensors & Bioelectronics 5:37-46.
Schuler et al. 1999. Modified gas-permeable silicone rubber membranes for covalent immobilisation of enzymes and their use in biosensor development. Analyst 124:1181-1184.
Selam, J. L. 1997. Management of diabetes with glucose sensors and implantable insulin pumps. From the dream of the 60s to the realities of the 90s. ASAIO J, 43:137-142.
Service et al. 1970. Mean amplitude of glycemic excursions, a measure of diabetic instability. Diabetes, 19: 644-655.
Service et al. 1987. Measurements of glucose control. Diabetes Care, 10: 225-237.
Sharkawy et al. 1996. Engineering the tissue which encapsulates subcutaneous implants. I. Diffusion properties, J Biomed Mater Res, 37:401-412.
Shaw et al. "In vitro testing of a simply constructed, highly stable glucose sensor suitable for implantation in diabetic patients," Biosensors & Bioelectronics, 6:401-406 (1991).
Shichiri et al. 1982. Wearable artificial endocrine pancrease with needle-type glucose sensor. Lancet 2:1129-1131.
Shichiri et al. 1983. Glycaemic Control in Pancreatectomized Dogs with a Wearable Artificial Endocrine Pancreas. Diabetologia 24:179-184.
Shichiri et al. 1985. Needle-type Glucose Sensor for Wearable Artificial Endocrine Pancreas in Implantable Sensors 197-210.
Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.
Shichiri et al. 1989. Membrane Design for Extending the Long-Life of an Implantable Glucose Sensor. Diab. Nutr. Metab. 2:309-313.
Shults et al. 1994. A telemetry-instrumentation system for monitoring multiple subcutaneously implanted glucose sensors. IEEE Transactions on Biomedical Engineering 41(10):937-942.
Sieminski et al. 2000. Biomaterial-microvasculature interactions. Biomaterials 21:2233-2241.

(56) References Cited

OTHER PUBLICATIONS

Skyler, J. S. 2000. The economic burden of diabetes and the benefits of improved glycemic control: The potential role of a continuous glucose monitoring system. Diabetes Technology & Therapeutics 2 Suppl 1:S7-12.
Slater-Maclean et al. 2008. Accuracy of glycemic measurements in the critically ill. Diab. Thechnol. & Therapeut., 10:169-177.
Sokol et al. 1980, Immobilized-enzyme rate-determination method for glucose analysis, Clin. Chem. 26(1):89-92.
Sriyudthsak et al. 1996. Enzyme-epoxy membrane based glucose analyzing system and medical applications. Biosens Bioelectron 11:735-742.
Steil et al. 2003. Determination of plasma glucose during rapid glucose excursions with a subcutaneous glucose sensor. Diabetes Technology & Therapeutics 5(1):27-31.
Stern et al., 1957. Electrochemical polarization: 1. A theoretical analysis of the shape of polarization curves, Journal of the Electrochemical Society, 104(1):56-63.
Sternberg et al. 1988. Study and Development of Multilayer Needle-type Enzyme-based Glucose Microsensors. Biosensors 4:27-40.
Sternberg et al. 1988. Covalent enzyme coupling on cellulose acetate membranes for glucose sensor development. Anal. Chem. 69:2781-2786.
Sternberg et al., Calibration problems of subcutaneous glucosensors when applied "in-situ" in man, Hom Metab Res. (1994) 26(11): 523-525.
Stokes. 1988. Polyether Polyurethanes: Biostable or Not? J. Biomat. Appl. 3:228-259.
Suh et al. 2002. Behavior of fibroblasts on a porous hyaluronic acid incorporated collagen matrix. Yonsei Medical Journal 43(2):193-202.
Sumino T. et al. 1998. Preliminary study of continuous glucose monitoring with a microdialysis technique. Proceedings of the IEEE, 20(4):1775-1778.
Takegami et al. 1992. Pervaporation of ethanol water mixtures using novel hydrophobic membranes containing polydimethylsiloxane, Journal of Membrance Science, 75(93-105).
Tanenberg et al. 2000. Continuous glucose monitoring system: A new approach to the diagnosis of diabetic gastroparesis. Diabetes Technology & Therapeutics, 2 Suppl 1:S73-80.
Tang et al. 1993. Fibrin(ogen) mediates acute inflammatory responses to biomaterials. J Exp Med 178:2147-2156.
Tang et al. 1995. Inflammatory responses to biomaterials. Am J Clin Pathol 103:466-471.
Tang et al. 1998. Mast cells mediate acute inflammatory responses to implanted biomaterials. Proc Natl Acad Sci U S A 95:8841-8846.
Thompson et al., In Vivo Probes: Problems and Perspectives, Department of Chemistry, University of Toronto, Canada, pp. 255-261, 1986.
Tibell et al. 2001. Survival of macroencapsulated allogeneic parathyroid tissue one year after transplantation in nonimmunosuppressed humans. Cell Transplant 10:591-9.
Tierney et al. 2000. Effect of acetaminophen on the accuracy of glucose measurements obtained with the GlucoWatch biographer. Diabetes Technol Ther 2:199-207.
Tierney et al. 2000. The GlucoWatch® biographer: A frequent, automatic and noninvasive glucose monitor. Ann. Med. 32:632-641.
Trecroci, D. 2002. A Glimpse into the Future—Continuous Monitoring of Glucose with a Microfiber. Diabetes Interview 42-43.
Tse and Gough. 1987. Time-Dependent Inactivation of Immobilized Glucose Oxidase and Catalase. Biotechnol. Bioeng. 29:705-713.
Turner and Pickup, "Diabetes mellitus: biosensors for research and management," Biosensors, 1:85-115 (1985).
Turner et al. 1984. Carbon Monoxide: Acceptor Oxidoreductase from *Pseudomonas thermocarboxydovorans* Strain C2 and its use in a Carbon Monoxide Sensor. Analytica Chimica Acta, 163: 161-174.
Turner, A.P.F. 1988. Amperometric biosensor based on mediator-modified electrodes. Methods in Enzymology 137:90-103.
Unger et al. 2004. Glucose control in the hospitalized patient. Emerg Med 36(9):12-18.
Updike et al. 1967. The enzyme electrode. Nature, 214:986-988.
Updike et al. 1982. Implanting the glucose enzyme electrode: Problems, progress, and alternative solutions. Diabetes Care, 5(3):207-212.
Updike et al. 1988. Laboratory Evaluation of New Reusable Blood Glucose Sensor. Diabetes Care, 11:801-807.
Updike et al. 1994. Enzymatic glucose sensor: Improved long-term performance in vitro and in vivo. ASAIO Journal, 40(2):157-163.
Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons.
Utah Medical Products Inc., Blood Pressure Transducers product specifications. 6 pp. 2003-2006, 2003.
Vadgama, P. Nov. 1981. Enzyme electrodes as practical biosensors. Journal of Medical Engineering & Technology 5(6):293-298.
Vadgama. 1988. Diffusion limited enzyme electrodes. NATO ASI Series: Series C, Math and Phys. Sci. 226:359-377.
Van den Berghe 2004. Tight blood glucose control with insulin in "real-life" intensive care. Mayo Clin Proc 79(8):977-978.
Velho et al. 1989. In vitro and in vivo stability of electrode potentials in needle-type glucose sensors. Influence of needle material. Diabetes 38:164-171.
Velho et al. 1989. Strategies for calibrating a subcutaneous glucose sensor. Biomed Biochim Acta 48(11/12):957-964.
von Woedtke et al. 1989. In situ calibration of implanted electrochemical glucose sensors. Biomed Biochim. Acta 48(11/12):943-952.
Wagner et al. 1998. Continuous amperometric monitoring of glucose in a brittle diabetic chimpanzee with a miniature subcutaneous electrode. Proc. Natl. Acad. Sci. A, 95:6379-6382.
Wang et al. 1994. Highly Selective Membrane-Free, Mediator-Free Glucose Biosensor. Anal. Chem. 66:3600-3603.
Wang et al. 1997. Improved ruggedness for membrane-based amperometric sensors using a pulsed amperometric method. Anal Chem 69:4482-4489.
Ward et al. 2004. A wire-based dual-analyte sensor for Glucose and Lactate: In Vitro and In Vivo Evaluation, Diab Tech Therapeut. 6(3): 389-401.
Ward et al. 2000. Understanding Spontaneous Output Fluctuations of an Amperometric Glucose Sensor: Effect of Inhalation Anesthesia and use of a Nonenzyme Containing Electrode. ASAIO Journal 540-546.
Ward et al. 2000. Rise in background current over time in a subcutaneous glucose sensor in the rabbit: Relevance to calibration and accuracy. Biosensors & Bioelectronics, 15:53-61.
Ward et al. 2002. A new amperometric glucose microsensor: In vitro and short-term in vivo evaluation. Biosensors & Bioelectronics, 17:181-189.
Wientjes, K. J. C. 2000. Development of a glucose sensor for diabetic patients (Ph.D. Thesis).
Wikipedia 2006. "Intravenous therapy," http://en.wikipedia.org/wiki/Intravenous_therapy, Aug. 15, 2006, 6 pp.
Wiley Electrical and Electronics Engineering Dictionary. 2004. John Wiley & Sons, Inc. pp. 141, 142, 548, 549.
Wilkins et al. 1988. The coated wire electrode glucose sensor, Horm Metab Res Suppl., 20:50-55.
Wilkins et al. 1995. Integrated implantable device for long-term glucose monitoring. Biosens. Bioelectron 10:485-494.
Wilkins et al. 1996. Glucose monitoring: state of the art and future possibilities. Med Eng Phys 18:273-288.
Wilson et al. 1992. Progress toward the development of an implantable sensor for glucose. Clin. Chem. 38(9):1613-1617.
Wilson et al. 2000. Enzyme-based biosensors for in vivo measurements. Chem. Rev., 100:2693-2704.
Wood, W. et al. Mar. 1990. Hermetic Sealing with Epoxy. Mechanical Engineering 1-3.
Woodward. 1982. How Fibroblasts and Giant Cells Encapsulate Implants: Considerations in Design of Glucose Sensor. Diabetes Care 5:278-281.
Wu et al. 1999. In situ electrochemical oxygen generation with an immunoisolation device. Annals New York Academy of Sciences, pp. 105-125.

(56) References Cited

OTHER PUBLICATIONS

Yamasaki et al. 1989. Direct measurement of whole blood glucose by a needle-type sensor. Clinica Chimica Acta. 93:93-98.

Yamasaki, Yoshimitsu. Sep. 1984. The development of a needle-type glucose sensor for wearable artificial endocrine pancreas. Medical Journal of Osaka University 35(1-2):25-34.

Yang et al (1996). "A glucose biosensor based on an oxygen electrode: In-vitro performances in a model buffer solution and in blood plasma," Biomedical Instrumentation & Technology, 30:55-61.

Yang et al. 1998. Development of needle-type glucose sensor with high selectivity. Science and Actuators B 46:249-256.

Yang, et al. 2004. A Comparison of Physical Properties and Fuel Cell Performance of Nafion and Zirconium Phosphate/Nafion Composite Membranes. Journal of Membrane Science 237:145-161.

Ye et al. 1993. High Current Density 'Wired' Quinoprotein Glucose Dehydrogenase Electrode. Anal. Chem. 65:238-241.

Zamzow et al. 1990. Development and evaluation of a wearable blood glucose monitor, ASAIO Transactions; 36(3): pp. M588-M591.

Zethelius et al. 2008. Use of multiple biomarkers to improve the prediction of death from cardiovascular causes. N. Engl. J. Med., 358: 2107-2116.

Zhang et al (1993). Electrochemical oxidation of H2O2 on Pt and Pt + Ir electrodes in physiological buffer and its applicability to H2O2-based biosensors. J. Electroanal. Chem., 345:253-271.

Zhang et al. 1993. In vitro and in vivo evaluation of oxygen effects on a glucose oxidase based implantable glucose sensor. Analytica Chimica Acta, 281:513-520.

Zhang et al. 1994. Elimination of the acetaminophen interference in an implantable glucose sensor. Analytical Chemistry 66(7):1183-1188.

Zhu et al. (1994). "Fabrication and characterization of glucose sensors based on a microarray H2O2 electrode." Biosensors & Bioelectronics, 9: 295-300.

Zhu et al. 2002. Planar amperometric glucose sensor based on glucose oxidase immobilized by chitosan film on prussian blue layer. Sensors, 2:127-136.

\* cited by examiner

DEVICE AND METHOD FOR DETERMINING ANALYTE LEVELS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 13/411,414, filed Mar. 2, 2012, which is a continuation of U.S. application Ser. No. 12/696,003, filed Jan. 28, 2010, now U.S. Pat. No. 8,155,723, which is a continuation of U.S. application Ser. No. 11/546,157, filed Oct. 10, 2006, now abandoned, which is a continuation of U.S. application Ser. No. 11/039,269, filed Jan. 19, 2005, now U.S. Pat. No. 7,136,689, which is a continuation of U.S. application Ser. No. 09/916,858, filed Jul. 27, 2001, now U.S. Pat. No. 6,862,465, which is a continuation-in-part of U.S. application Ser. No. 09/447,227, filed Nov. 22, 1999, which is a divisional of U.S. application Ser. No. 08/811,473, filed Mar. 4, 1997, now U.S. Pat. No. 6,001,067.

FIELD OF THE INVENTION

The present invention relates generally to devices and methods for determining analyte levels, and, more particularly, to implantable devices and methods for monitoring glucose levels in a biological fluid.

BACKGROUND OF THE INVENTION

The continuous measurement of substances in biological fluids is of interest in the control and study of metabolic disorders. Electrode systems have been developed for this purpose whereby an enzyme-catalyzed reaction is monitored (e.g., by the changing concentrations of reactants or products) by an electrochemical sensor. In such electrode systems, the electrochemical sensor comprises an electrode with potentiometric or amperometric function in close contact with a thin layer containing an enzyme in dissolved or insoluble form. Generally, a semipermeable membrane separates the thin layer of the electrode containing the enzyme from the sample of biological fluid that includes the substance to be measured.

Electrode systems that include enzymes have been used to convert amperometrically inactive substances into reaction products that are amperometrically active. For example, in the analysis of blood for glucose content, glucose (which is relatively inactive amperometrically) may be catalytically converted by the enzyme glucose oxidase in the presence of oxygen and water to gluconic acid and hydrogen peroxide. Tracking the concentration of glucose is thereby possible since for every glucose molecule reacted a proportional change in either oxygen or hydrogen peroxide sensor current will occur [U.S. Pat. Nos. 4,757,022 and 4,994,167 to Shults et al., both of which are hereby incorporated by reference]. Hydrogen peroxide is anodically active and produces a current that is proportional to the concentration of hydrogen peroxide. [Updike et al., Diabetes Care, 11:801-807 (1988)].

Despite recent advances in the field of implantable glucose monitoring devices, presently used devices are unable to provide data safely and reliably for long periods of time (e.g., months or years) [See, e.g., Moatti-Sirat et al., Diabetologia 35:224-30 (1992)]. For example, Armour et al., Diabetes 39:1519-26 (1990), describes a miniaturized sensor that is placed intravascularly, thereby allowing the tip of the sensor to be in continuous contact with the blood. Unfortunately, probes that are placed directly into the vasculature put the recipient at risk for thrombophlebosis, thromboembolism, and thrombophlebitis.

Currently available glucose monitoring devices that may be implanted in tissue (e.g., subcutaneously) are also associated with several shortcomings. For example, there is no dependable flow of blood to deliver sample to the tip of the probe of the implanted device. Similarly, in order to be effective, the probe must consume some oxygen and glucose, but not enough to perturb the available glucose which it is intended to measure; subcutaneously implanted probes often reside in a relatively low oxygen environment in which oxygen or glucose depletion zones around the probe tip may result in erroneously low measured glucose levels. In addition, implantable devices that utilize electrode sensors require membranes of the appropriate composition to protect the sensor from harsh in vivo environmental conditions. Current membrane technology has allowed the development of a single structural membrane that performs the same functions that previously required multiple membranes. However, these single membranes have been observed to delaminate and thus prevent accurate long-term glucose monitoring. Finally, the probe may be subject to "motion artifact" because the device is not adequately secured to the tissue, thus contributing to unreliable results. Partly because of these limitations, it has previously been difficult to obtain accurate information regarding the changes in the amounts of analytes (e.g., whether blood glucose levels are increasing or decreasing); this information is often extremely important, for example, in ascertaining whether immediate corrective action is needed in the treatment of diabetic patients.

There is a need for a device that accurately and continuously determines the presence and the amounts of a particular analyte, such as glucose, in biological fluids. The device should be easy to use, be capable of accurate measurement of the analyte over long periods of time, and should not readily be susceptible to motion artifact.

SUMMARY OF THE INVENTION

The present invention relates generally to devices and methods for determining analyte levels, and, more particularly, to implantable devices and methods for monitoring glucose levels in a biological fluid.

In one aspect of the present invention, an implantable device for measuring an analyte in a biological fluid is provided, which includes the following: a housing including an electronic circuit; and a sensor operably connected to the electronic circuit of the housing, the sensor including i) a member for determining the amount of glucose in a biological sample ii) a bioprotective membrane, the bioprotective membrane positioned more distal to the housing than the glucose determining member and substantially impermeable to macrophages, and iii) an angiogenic layer, the angiogenic layer positioned more distal to the housing than the bioprotective membrane.

The present invention further encompasses a method of monitoring glucose levels, the method including the steps of providing a host, and an implantable device as described above and implanting the device in the host under conditions such that the device measures glucose for a period exceeding 360 days.

In one embodiment of this aspect, the invention encompasses a method of measuring glucose in a biological fluid that includes the steps of providing a host, and an implantable device as provided above, wherein the glucose determining member of the implantable device is capable of continuous glucose sensing, and implanting the device in the host.

DEFINITIONS

In order to facilitate an understanding of the present invention, a number of terms are defined below.

The term "accurately" means, for example, 95% of measured values within 25% of the actual value as determined by analysis of blood plasma, preferably within 15% of the actual value, and most preferably within 5% of the actual value. Alternatively, "accurately" means that 85% of the measured values fall into the A and B regions of a Clarke error grid, or preferably 90%, or most preferably 95% of the measured values fall into these regions. It is understood that like any analytical device, calibration, calibration validation and recalibration are required for the most accurate operation of the device.

The term "analyte" refers to a substance or chemical constituent in a biological fluid (e.g., blood or urine) that can be analyzed. A preferred analyte for measurement by the devices and methods of the present invention is glucose.

The terms "sensor interface," "sensor means," "sensor" and the like refer to the region of a monitoring device responsible for the detection of a particular analyte. For example, in some embodiments of a glucose monitoring device, the sensor interface refers to that region wherein a biological sample (e.g., blood or interstitial fluid) or a portion thereof contacts (directly or after passage through one or more membranes or layers) an enzyme (e.g., glucose oxidase); the reaction of the biological sample (or portion thereof) results in the formation of reaction products that allow a determination of the glucose level in the biological sample. In preferred embodiments of the present invention, the sensor means comprises an angiogenic layer, a bioprotective layer, an enzyme layer, and an electrolyte phase (i.e., a free-flowing liquid phase comprising an electrolyte-containing fluid [described further below]). In some preferred embodiments, the sensor interface protrudes beyond the plane of the housing.

The term "tissue interface" refers to that region of a monitoring device that is in contact with tissue.

The terms "operably connected," "operably linked," and the like refer to one or more components being linked to another component(s) in a manner that allows transmission of, e.g., signals between the components. For example, one or more electrodes may be used to detect the amount of analyte in a sample and convert that information into a signal; the signal may then be transmitted to electronic circuit means (i.e., the electrode is "operably linked" to the electronic circuit means), which may convert the signal into a numerical value in the form of known standard values.

The term "electronic circuit means" or "electronic circuit" refers to the electronic circuitry components of a biological fluid measuring device required to process information obtained by a sensor means regarding a particular analyte in a biological fluid, thereby providing data regarding the amount of that analyte in the fluid. U.S. Pat. No. 4,757,022 to Shults et al., previously incorporated by reference, describes suitable electronic circuit means (see, e.g., FIG. 7); of course, the present invention is not limited to use with the electronic circuit means described therein. A variety of circuits are contemplated, including but not limited to those circuits described in U.S. Pat. Nos. 5,497,772 and 4,787,398, hereby incorporated by reference.

The terms "angiogenic layer," "angiogenic membrane," and the like refer to a region, membrane, etc. of a biological fluid measuring device that promotes and maintains the development of blood vessels microcirculation around the sensor region of the device. As described in detail below, the angiogenic layer of the devices of the present invention may be constructed of membrane materials alone or in combination such as polytetrafluoroethylene, hydrophilic polyvinylidene fluoride, mixed cellulose esters, polyvinylchloride, and other polymers including, but not limited to, polypropylene, polysulfone, and polymethylmethacrylate.

The phrase "positioned more distal" refers to the spatial relationship between various elements in comparison to a particular point of reference. For example, some embodiments of a biological fluid measuring device comprise both a bioprotective membrane and an angiogenic layer/membrane. If the housing of the biological fluid measuring device is deemed to be the point of reference and the angiogenic layer is positioned more distal to the housing than the bioprotective layer, then the bioprotective layer is closer to the housing than the angiogenic layer.

The terms "bioprotective membrane," "bioprotective layer," and the like refer to a semipermeable membrane comprised of protective biomaterials of a few microns thickness or more that are permeable to oxygen and glucose and are placed over the tip of the sensor to keep the white blood cells (e.g., tissue macrophages) from gaining proximity to and then damaging the enzyme membrane. In some embodiments, the bioprotective membrane has pores (typically from approximately 0.1 to approximately 1.0 micron). In preferred embodiments, a bioprotective membrane comprises polytetrafluoroethylene and contains pores of approximately 0.4 microns in diameter. Pore size is defined as the pore size provided by the manufacturer or supplier.

The phrase "substantially impermeable to macrophages" means that few, if any, macrophages are able to cross a barrier (e.g., the bioprotective membrane). In preferred embodiments, fewer than 1% of the macrophages that come in contact with the bioprotective membrane are able to cross.

The phrase "material for securing said device to biological tissue" refers to materials suitable for attaching the devices of the present invention to, the fibrous tissue of a foreign body capsule. Suitable materials include, but are not limited to, poly(ethylene terephthalate). In preferred embodiments, the top of the housing is covered with the materials in the form of surgical grade fabrics; more preferred embodiments also contain material in the sensor interface region (see FIG. 1B).

The phrase "member for determining the amount of glucose in a biological sample" refers broadly to any mechanism (e.g., enzymatic or non-enzymatic) by which glucose can be quantitated. For example, some embodiments of the present invention utilize a membrane that contains glucose oxidase that catalyzes the conversion of glucose to gluconate: Glucose+$O_2$=Gluconate+$H_2O_2$. Because for each glucose molecule converted to gluconate, there is a proportional change in the co-reactant $O_2$ and the product $H_2O_2$, one can monitor the current change in either the co-reactant or the product to determine glucose concentration.

The phrase "apparatus for transmitting data to a location external to said device" refers broadly to any mechanism by which data collected by a biological fluid measuring device implanted within a subject may be transferred to a location external to the subject. In preferred embodiments of the present invention, radiotelemetry is used to provide data regarding blood glucose levels, trends, and the like.

The terms "radiotelemetry," "radiotelemetric device," and the like refer to the transmission by radio waves of the data recorded by the implanted device to an ex vivo recording station (e.g., a computer), where the data is recorded and, if desired, further processed (see, e.g., U.S. Pat. Nos. 5,321,414 and 4,823,808, hereby incorporated by reference; PCT Pat. Publication WO 94/22367).

The term "host" refers to both humans and animals.

The phrase "continuous glucose sensing" refers to the period in which monitoring of plasma glucose concentration is continuously carried out. More specifically, at the beginning of the period in which continuous glucose sensing is effected, the background sensor output noise diminishes and the sensor output stabilizes (e.g., over several days) to a long-term level reflecting adequate microcirculatory delivery of glucose and oxygen to the tip of the sensor (see FIG. 2).

The term "filtrate layer" refers to any permeable membrane that is able to limit molecules from passing through the membrane based on their properties including molecular weight. More particularly, the resistance layer, interference layer and bioprotective membrane are examples of layers that can function as filtrate layers, depending on the materials from which they are prepared. These layers can control delivery of analyte to a sensing means. Furthermore, these layers can reduce a number of undesirable molecular species that may otherwise be exposed to the sensor for detection and provide a controlled sample volume to the analyte sensing means.

DETAILED DESCRIPTION OF THE INVENTION

Figure 1A:
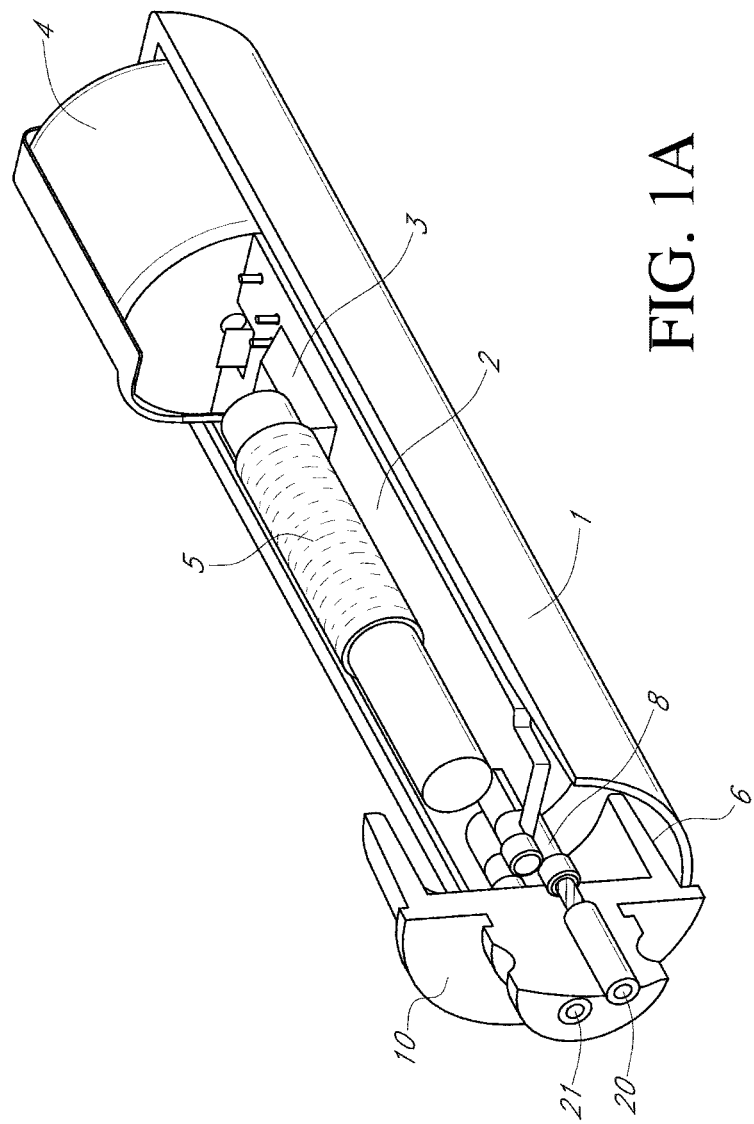
FIG. 1A depicts a cross-sectional drawing of one embodiment of an implantable analyte measuring device of the present invention.

The present invention relates generally to devices and methods for determining analyte levels, and, more particularly, to implantable devices and methods for monitoring glucose levels in a biological fluid. In a preferred embodiment, the device and methods of the present invention are used to determine the level of glucose in a host, a particularly important measurement for individuals having diabetes.

Although the description that follows is primarily directed at glucose monitoring devices and methods for their use, the devices and methods of the present invention are not limited to glucose measurement. Rather, the devices and methods may be applied to detect and quantitate other analytes present in biological fluids (including, but not limited to, amino acids and lactate), especially those analytes that are substrates for oxidase enzymes [see, e.g., U.S. Pat. No. 4,703,756 to Gough et al., hereby incorporated by reference]. Moreover, the devices and methods of the present invention may be utilized to present components of biological fluids to measurement methods which are not enzyme-based, including, but not limited to, those based on surface plasmon resonance, surface acoustic waves, optical absorbance in the long wave infrared region, and optical rotation of polarized light.

For example, surface plasmon resonance sensors that analyze a region within less than one wavelength of analysis light near the flat surface of the sensor have been described (See U.S. Pat. No. 5,492,840). These sensors have been used, for example, in the study of immunochemistry and other surface bound chemical reactions (Jonsson et al., Annales de Biologies Clinique 51 (10:19, 1993). This type of sensor may be incorporated into the implantable device of the present invention for the detection of a number of different analytes including glucose. One skilled in the art would recognize that the surface plasmon resonance sensor is an optical sensor and that the implantable device of the present invention may further include a source of coherent radiation (e.g. a laser operating in the visible or near infrared).

In one application, referred to here as a consumptive approach, an enzyme that consumes the analyte producing a detectable product is immobilized on the sensor in the filtrate layer. When the enzyme consumes the analyte, the reaction products diffuse away from the enzyme at a rate dependent on the permeability of the layers distal to the enzyme layer. As a result, reaction products will accumulate at a higher concentration near the sensor, within one wavelength of analysis light, where they may be detected and measured. One example of such a system that detects the presence of glucose would immobilize a glucose oxidase enzyme layer on the sensor surface.

The layers of the present invention play an important role in the effective operation and function of this type of sensor. In particular, the angiogenic layer assures a constant supply of analyte from the tissues of the subject, the bioprotective membrane protects the underlying layers from cellular attack, the resistance layer controls the rate of delivery of analyte and the filtrate layer performs many functions including; providing a low molecular weight filtrate, reducing the number of undesirable molecular species available to the sensor for detection and providing a controlled volume of sample for detection by the sensor. As mentioned above, the bioprotective membrane, resistance layer and interference layer can function as filtrate layers. For example, it is well within the contemplation of the present invention that the bioprotective membrane can be made of a material that is able to exclude certain molecules from passing through the membrane based on their size.

One skilled in the art would recognize that the reaction kinetics associated with each type of enzyme that may be selected for use with this sensor is unique. However, in general, if an excess of enzyme is provided, the enzyme turnover rate is proportional to the flux of analyte to the enzyme and independent of the enzyme concentration. Therefore, the actual analyte concentration may be calculated utilizing the diffusion rate of the detectable analyte across the bioprotective resistance layers.

In another application, referred to here as a non-consumptive approach, an analyte-binding compound is provided on the surface plasmon resonance sensor surface within one wavelength of analysis light. This compound reversibly binds, but does not consume, the analyte. In this application, the analyte moves reversibly onto and off of attachment sites on the binding compound. This reaction provides a steady state condition for bound and unbound analyte that may be quantitated and analyte concentration mathematically calculated. One skilled in the art would recognize that the reaction kinetics associated with binding and release of the analyte is unique for each type of binding compound selected.

Examples of such a system that detects the presence of glucose provide a binding compound comprised of conconavalin A or a wide range of borate containing compounds (See U.S. Pat. No. 6,011,985).

Since this is a chemical equilibrium-based approach, a filtrate layer is not necessarily required to maintain an analyte concentration near the sensor. However, such a membrane would still be desired to reduce the number of undesirable molecular species available to the analyte-binding layer. Preferably, the bioprotective layer is thin to allow rapid sensor equilibration to changes in analyte levels. As described above, one skilled in the art would recognize that the function of the filtrate layer could be incorporated into the bioprotective membrane by selection of the appropriate molecular exclusion, such as exclusion by molecular weight, if desired.

A variety of materials may be utilized to construct a combination angiogenic/bioprotective membrane, many of which are described below under the angiogenic layer and bioprotective membrane headings. Preferably, this combination membrane is ePTFE embedded in a layer of PVP containing urethane hydrogel. However, any material that performs a similar function as the PVP containing polyurethane hydrogel could be substituted.

In either application, consumptive or non-consumptive, one skilled in the art would recognize that the response time of the sensor is subject to Fick's law of diffusion. More specifically, sensors with thick membrane layers or that have low analyte diffusivity will respond slower to change in analyte concentration than sensors with thin membranes or that have high analyte diffusivity. Consequently, reasonable optimization experimentation with the membrane and layers would be required to meet various use requirements.

One skilled in the art would further recognize that the consumptive or non-consumptive approaches of the previous example could be applied to additional sensor modalities as follows:

1. Another sensor that may be incorporated into the device of the present invention that has been previously described is a surface acoustic wave sensor (See U.S. Pat. No. 5,932,953). This sensor, also referred to as a bulk-acoustic wave piezoelectric resonator, typically includes a planar surface of piezoelectric material with two respective metal layers bonded on opposite sides that form the electrodes of the resonator. The two surfaces of the resonator are free to undergo vibrational movement when the resonator is driven by a signal within the resonance band of the resonator. One of these surfaces is adapted to provide reversible binding sites for the analyte being detected. The binding of the analyte on the surface of the resonator alters the resonant characteristics of the resonator and changes in the resonant characteristics may be detected and interpreted to provide quantitative information regarding the analyte concentration.

2. Another sensor that may be incorporated into the device of the present invention is an optical absorbance sensor (See U.S. Pat. No. 6,049,727). This sensor utilizes short to medium wavelength infrared light that is passed through a sample with the unabsorbed infrared light being monitored by an optical detector.

Previously developed methods for analysis of analytes such as glucose in tissues and blood have been relatively unsuccessful for two reasons, interference from other chemicals present in the complex biological sample and signal variation due to poor control of sample volume. These problems may be solved by providing a low molecular weight filtrate of biological fluid in a controlled volume of sample to the sensor. In one system of the present invention, biological analyte is provided to the sensor through the angiogenic layer. This analyte is then filtered through the bioprotective membrane to produce a desirable filtrate. Alternatively, a third filtrate layer, such as an interference layer, may be utilized having specific filtration properties to produce the desired filtrate. The three-dimensional structure of the bioprotective membrane and/or other filtrate layers is utilized to define and stabilize the sample volume. One skilled in the art would recognize that any material that provides a low molecular weight filtrate to the sensor in a controlled volume might be utilized. Preferably, this material is polyurethane.

The sensor may be enhanced by partial metallization of the distal side of the filtrate producing material that would serve to isolate by reflection the optical signal to the space within the filtrate region directly adjacent to the sensor. This metal film may be a durable metal including, but not restricted to, gold or platinum and may be vacuum deposited onto the filtrate producing material.

One skilled in the art would recognize that the optical absorbance sensor requires a source of short to medium wavelength infrared light. Consequently, the implantable device of the present invention would further include a source of infrared radiation and an optical detector.

3. Another sensor that may be incorporated into the device of the present invention that has been previously described is a polarized light optical rotation sensor (See U.S. Pat. No. 5,209,231). This sensor may be used to detect an analyte that rotates polarized light such as glucose. In particular, glucose concentrations in biological fluids in the range of 0.05 to 1.00% w/v may be detected and quantitated. Normal non-diabetic subjects generally have biological glucose concentrations ranging from 0.07 to 0.12% w/v.

In this type of sensor, the optical detector receives polarized light passed through a biological sample and then further through a polarizing filter. The optical activity of an analyte in the sample rotates the polarized light in proportion to its concentration. Unfortunately, accurate measurements of glucose in complex biological samples has proven difficult because of the optical activity of interfering substances and poor control of sample volume. These problems may be solved by providing a low molecular weight filtrate of biological fluid in a controlled volume to the sensor. The present invention meets this criterion by providing a continuous supply of biological glucose to the sensor through the angiogenic layer that is filtered through a bioprotective membrane and/or a filtrate layer as described previously for the optical absorbance sensor. One skilled in the art would recognize that any material that provides a low molecular weight filtrate to the sensor in a controlled geometry might be utilized. Preferably, this material is polyurethane. In addition, one skilled in the art would recognize that the polarized light optical rotation sensor requires a source of polarized light. Consequently, the implantable device of the present invention would further include a source of polarized radiation.

4. Another sensor that may be incorporated into the device of the present invention that has been previously described is a fluorescence sensor (See U.S. Pat. No. 5,341,805). The invention of Colvin provides a method for incorporating an ultraviolet light source and fluorescent sensing molecules in an implantable device. However, Colvin does not describe how the sensor would survive harsh in vivo environmental conditions, how the device would be functionally integrated into body tissues or how a continuous supply of glucose would be maintained for detection by the sensor. These problems may be solved by providing a low molecular weight filtrate of biological fluid in a controlled volume to the sensor.

In this example, a continuous supply of biological glucose passes to the sensor through the angiogenic layer that prevents isolation of the sensor by the body tissue. The glucose is then filtered through the bioprotective membrane to produce a desirable filtrate having fewer interfering molecules and to protect the sensor from in vivo environmental conditions. Alternatively, a filtrate layer may be utilized having specific filtration properties to produce the desired filtrate. The three-dimensional structure of the bioprotective membrane and/or filtrate layer also provides stabilized sample volume for detection by the sensor.

One skilled in the art would recognize that a fluorescence sensor requires a source of light. Consequently, the implantable device of the present invention would further comprise a source of radiation, as well as fluorescent sensing molecules to detect the presence of analyte.

I. NATURE OF THE FOREIGN BODY CAPSULE

Devices and probes that are implanted into subcutaneous tissue will almost always elicit a foreign body capsule (FBC) as part of the body's response to the introduction of a foreign material. Therefore, implantation of a glucose sensor results in an acute inflammatory reaction followed by building of fibrotic tissue. Ultimately, a mature FBC including primarily a vascular fibrous tissue forms around the device (Shanker and Greisler, Inflammation and Biomaterials in Greco R S, ed. Implantation Biology: The Host Response and Biomedical Devices, pp 68-80, CRC Press (1994)).

Although fluid is frequently found within the capsular space between the sensor and the capsule, levels of analytes (e.g., glucose and oxygen) within the fluid often do not mimic levels in the body's vasculature, making accurate measurement difficult.

Figure 2:
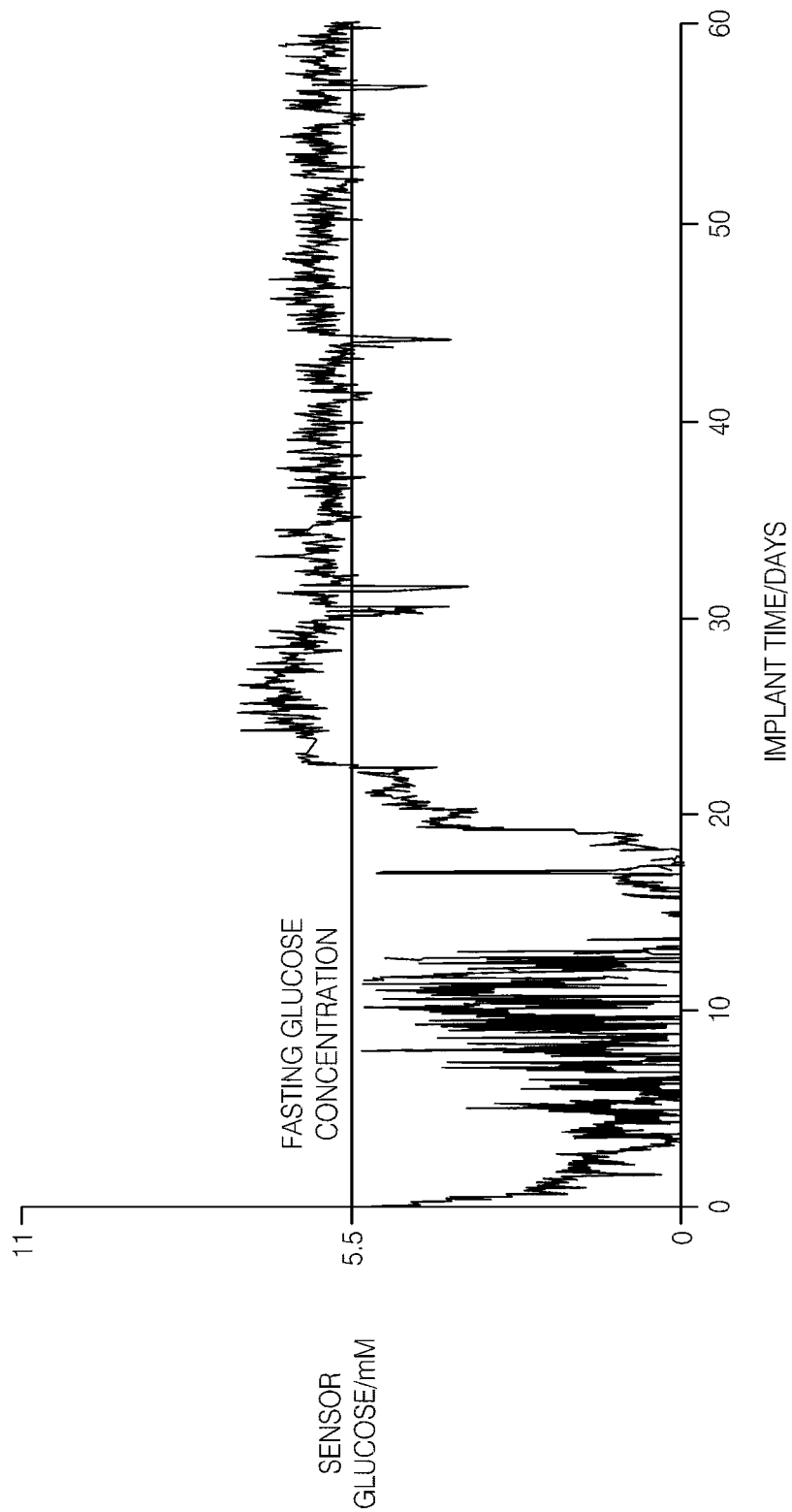
FIG. 2 graphically depicts glucose levels as a function of the number of days post-implant.

In general, the formation of a FBC has precluded the collection of reliable, continuous information, reportedly because of poor vascularization, the composition of a FBC has prevented stabilization of the implanted device, contributing to motion artifact that renders unreliable results. Thus, conventionally, it has been the practice of those skilled in the art to attempt to minimize FBC formation by, for example, using a short-lived needle geometry or sensor coatings to minimize the foreign body reaction ("Biosensors in the Body" David M. Fraser, ed.; 1997 pp 117-170. Wiley & Sons Ltd., West Sussex, England), In contrast to the prior art, the teachings of the present invention recognize that FBC formation is the dominant event surrounding long term implantation of any sensor and must be orchestrated to support rather than hinder or block sensor performance. For example, sensors often do not perform well until the FBC has matured sufficiently to provide ingrowth of well-attached tissue bearing a rich supply of capillaries directly to the surface of the sensor. With reference to FIG. 2, stabilization of device function generally occurs between about 2 and 8 weeks depending on the rate of healing and formation of new capillaries. In some cases, devices are functional from the time of implant, and sometimes it may take as long as 12 weeks. However, the majority of devices begin functioning between weeks 2 and 8 after implantation. This maturation process, when initiated according to the present invention, is a function of biomaterial and host factors that initiate and modulate angiogenesis, and promote and control fibrocyte ingrowth. The present invention contemplates the use of particular materials to promote angiogenesis adjacent to the sensor interface (also referred to as the electrode-membrane region, described below) and to anchor the device within the FBC.

II. THE IMPLANTABLE GLUCOSE MONITORING DEVICE OF THE PRESENT INVENTION

The present invention contemplates the use of a unique micro-geometry at the sensor interface of an implantable device. Moreover, the present invention contemplates the use of materials covering all or a portion of the device to assist in the stabilization of the device following implantation. However, it should be pointed out that the present invention does not require a device comprising particular electronic components (e.g., electrodes, circuitry, etc). Indeed, the teachings of the present invention can be used with virtually any monitoring device suitable for implantation (or subject to modification allowing implantation); suitable devices include, but are not limited to, those described in U.S. Pat. No. 6,001,067 to Shults et al.; U.S. Pat. No. 4,703,756 to Gough et al., and U.S. Pat. No. 4,431,004 to Bessman et al.; the contents of each being hereby incorporated by reference, and Bindra et al., Anal. Chem. 63:1692-96 (1991).

In the discussion that follows, an example of an implantable device that includes the features of the present invention is first described. Thereafter, the specific characteristics of, for example, the sensor interface contemplated by the present invention will be described in detail.

Generally speaking, the implantable devices contemplated for use with the present invention are cylindrical or oval shaped; of course, devices with other shapes may also be used with the present invention. The sample device includes a housing composed of radiotransparent ceramic. FIG. 1A depicts a cross-sectional drawing of one embodiment of an implantable measuring device. Referring to FIG. 1A, the cylindrical device includes a ceramic body 1 and ceramic head 10 houses the sensor electronics that include a circuit board 2, a microprocessor 3, a battery 4, and an antenna 5. Furthermore, the ceramic body 1 and head 10 possess a matching taper joint 6 that is sealed with epoxy. The electrodes are subsequently connected to the circuit board via a socket 8.

Figure 1B:
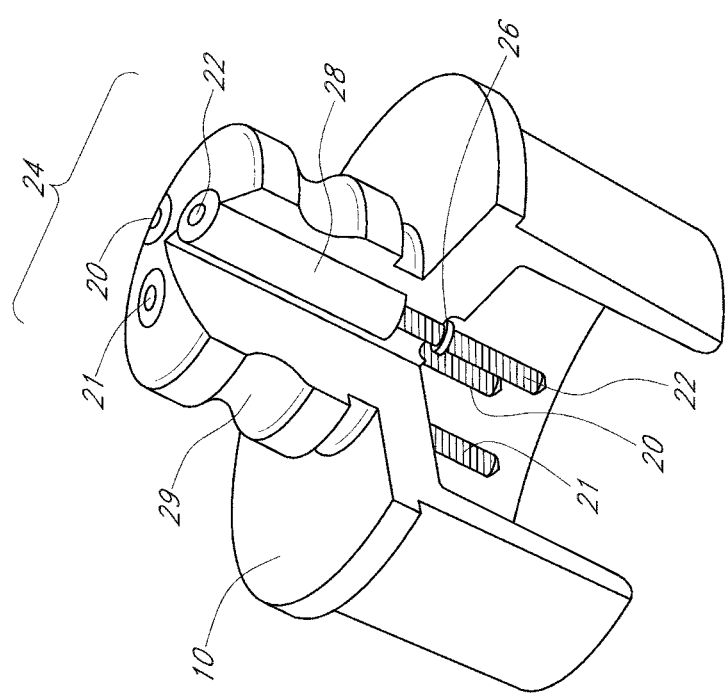
FIG. 1B depicts a cross-sectional exploded view of the sensor interface dome of FIG. 1A.

As indicated in detail in FIG. 1B, three electrodes protrude through the ceramic head 10, a platinum working electrode 21, a platinum counter electrode 22 and a silver/silver chloride reference electrode 20. Each of these is hermetically brazed 26 to the ceramic head 10 and further affixed with epoxy 28. The sensing region 24 is covered with the sensing membrane described below and the ceramic head 10 contains a groove 29 so that the membrane may be affixed into place with an o-ring.

In a preferred embodiment, the device is cylindrical, as shown in FIG. 1A, and is approximately 1 cm in diameter, and 5.5 cm long. The sensing region is situated at one extreme end of the cylinder. The sensor region includes a dome onto which the sensing membranes are attached.

Maintaining the blood supply near an implanted foreign body like an implanted analyte-monitoring sensor requires stable fixation of FBC tissue on the surface of the foreign body. This can be achieved, for example, by using capsular attachment (anchoring) materials (e.g., those materials that includes the sensor interface and tissue anchoring layers) developed to repair or reinforce tissues, including, but not limited to, polyester (DACRON®; DuPont; poly(ethylene terephthalate)) velour, expanded polytetrafluoroethylene (TEFLON/®; Gore), polytetrafluoroethylene felts, polypropylene cloth, and related porous implant materials. In a preferred embodiment, porous silicone materials are used for anchoring the device. In another embodiment, non-woven polyester fibers are used for anchoring the device. Tissue tends to aggressively grow into the materials disclosed above and form a strong mechanical bond (i.e., tissue anchoring); this fixation of the implant in its capsule is essential to prevent motion artifact or disturbance of the newly developed capillary blood supply.

In a preferred embodiment, the anchoring material is attached directly to the body of the device. In the case of non-woven polyester fibers, they may be sutured into place by rolling the material onto the circumferential periphery of the device and further encircling the membrane with PTFE sutures and tying the sutures to hold the membrane in place. In another preferred embodiment, porous silicone is attached to the surface of the cylindrical device using medical grade silicone adhesive. In either case, the material may be further held in place by an o-ring (FIG. 1B).

As shown in FIG. 1A, the interior of the housing contains one or more batteries 4 operably connected to an electronic circuit means (e.g., a circuit board 2), which, in turn, is operably connected to at least one electrode (described below); in another embodiment, at least two electrodes are carried by the housing. In a preferred embodiment, three electrodes are used. Any electronic circuitry and batteries that render reliable, continuous, long-term (e.g., months to years) results may be used in conjunction with the devices of the present invention.

The housing of the devices of the present invention preferably contain a biocompatible ceramic material. A preferred embodiment of the device contains a radiofrequency transmitter and antenna within the body of the ceramic device. Ceramic materials are radiotransparent and, therefore, are preferred over metals that are radioopaque. Ceramic materials are preferred over plastic materials (which may also be radiotransparent) because they are more effective than plastics at preventing water penetration. In one embodiment of the invention, the ceramic head and body are connected at an approximately 0.9 cm long taper joint sealed with epoxy. In other embodiments, the head and body may be attached by sealing with metals to produce a completely hermetic package.

Figure 1C:
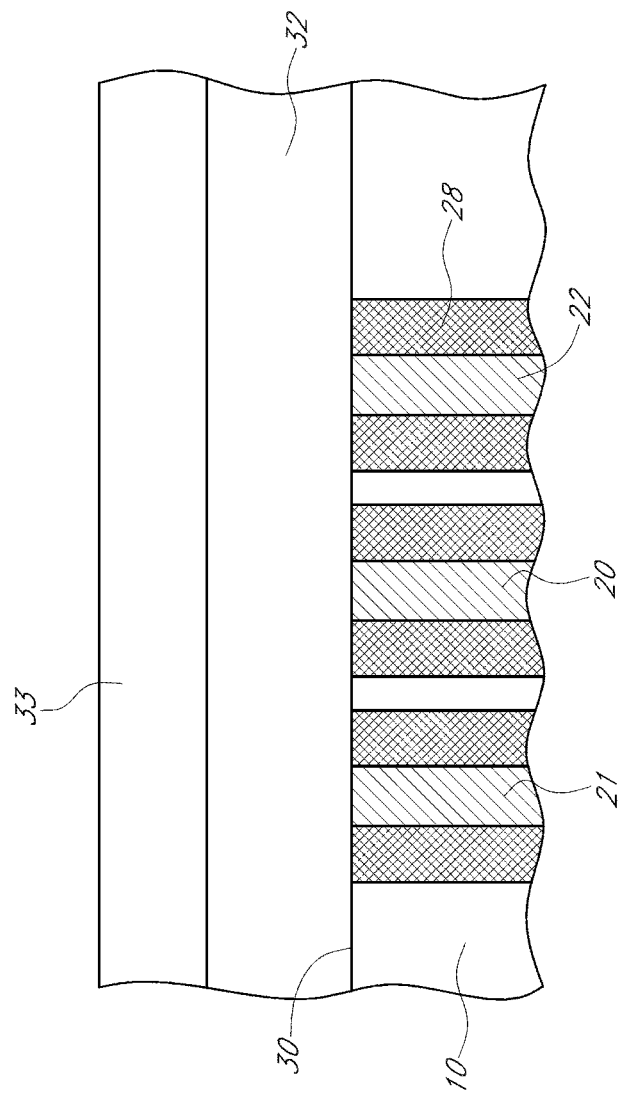
FIG. 1C depicts a cross-sectional exploded view of the electrode-membrane region of FIG. 1B detailing the sensor tip and the functional membrane layers.

FIG. 1C depicts a cross-sectional exploded view of the electrode-membrane region 24 set forth in FIG. 1B detailing the sensor tip and the functional membrane layers. As depicted in FIG. 1C, the electrode-membrane region includes several different membrane layers, the compositions and functions of which are described in detail below. The top ends of the electrodes are in contact with the electrolyte phase 30, a free-flowing fluid phase. The electrolyte phase is covered by the sensing membrane 32 that contains an enzyme, e.g., glucose oxidase, and several functional polymer layers (as described below). In turn, a composite bioprotective/angiogenic membrane 33 covers the sensing membrane 32 and serves, in part, to protect the sensor from external forces that may result in environmental stress cracking of the sensing membrane 32.

In one preferred embodiment of the inventive device, each of the membrane layers is affixed to the ceramic head 10 in FIGS. 1A and 1B by an o-ring. The o-ring may be formed of fluoroelastomer.

The present invention contemplates the construction of the membrane layers of the sensor interface region using standard film coating techniques. This type of membrane fabrication facilitates control of membrane properties and membrane testing.

III. THE SENSOR INTERFACE REGION

As mentioned above and disclosed in FIG. 1C, in a preferred embodiment, the sensor interface region includes several different layers and membranes that cover the electrodes of an implantable analyte-measuring device. The characteristics of these layers and membranes are now discussed in more detail. The layers and membranes prevent direct contact of the biological fluid sample with the electrodes, while permitting selected substances (e.g., analytes) of the fluid to pass therethrough for electrochemical reaction with the electrodes.

Measurement of analyte in a filtrate of biological fluid samples has been shown to be preferred over direct measurement of analyte in biological fluid in order to minimize effects of interfering substances and improve control of sample volume. It is well known in the art that electrode surfaces exposed to a wide range of biological molecules will suffer poisoning of catalytic activity and failure. However, utilizing the layers and membranes of the present invention, the active electrochemical surfaces of the sensor electrodes are preserved, allowing activity to be retained for extended periods of time in vivo. By limiting exposure of the platinum sensor surface to certain molecular species (e.g., molecules having a molecular weight below 34 Daltons, the molecular weight of hydrogen peroxide), in vivo sensor operating life in excess of one year in canine subjects has been observed.

A. Angiogenic Layer

For implantable glucose monitoring devices, a sensor/tissue interface must be created which provides the sensor with oxygen and glucose concentrations comparable to that normally available to tissue comprised of living cells. Absent such an interface, the sensor is associated with unstable and chaotic performance indicating that inadequate oxygen and/or glucose are reaching the sensor. The development of interfaces in other contexts has been reported. For example, investigators have developed techniques that stimulate and maintain blood vessels inside a FBC to provide for the demanding oxygen needs of pancreatic islets within an implanted membrane. [See, e.g., Brauker et al., J. Biomed. Mater. Res. (1995) 29:1517-1524]. These techniques depend, in part, on the use of a vascularizing layer on the exterior of the implanted membrane. However, previously described implantable analyte-monitoring devices have not been able to successfully maintain sufficient blood flow to the sensor interface.

As described above, the outermost layer of the electrode-membrane region includes an angiogenic material. The angiogenic layer of the devices of the present invention may be constructed of membrane materials such as hydrophilic polyvinylidene fluoride (e.g., Durapore®; Millipore Bedford, Mass.), mixed cellulose esters (e.g., MF; Millipore Bedford, Mass.), polyvinyl chloride (e.g., PVC; Millipore Bedford, Mass.), and other polymers including, but not limited to, polypropylene, polysulphone, and polymethylmethacrylate. Preferably, the thickness of the angiogenic layer is about 10 μm to about 20 μm. The angiogenic layer comprises pores sizes of about 0.5 μm to about 20 μm, and more preferably about 1.0 μm to about 10 μm, sizes that allow most substances to pass through, including, e.g., macrophages. The preferred material is expanded PTFE of a thickness of about 15 μm and pore sizes of about 5 μm to about 10 μm.

To further promote stable foreign body capsule structure without interfering with angiogenesis, an additional outermost layer of material comprised of a thin low-density non-woven polyester (e.g., manufactured by Reemay) can be laminated over the preferred PTFE described above. In preferred embodiments, the thickness of this layer is about 120 μm. This additional thin layer of material does not interfere with angiogenesis and enhances the manufacturability of the angiogenic layer. [See U.S. Pat. No. 5,741,330 to Brauker et al., hereby incorporated by reference; also U.S. Pat. No. 5,782,912, U.S. Pat. No. 5,800,529, U.S. Pat. No. 5,882,354 U.S. Pat. No. 5,964,804 assigned to Baxter].

B. Bioprotective Membrane

The inflammatory response that initiates and sustains a FBC is associated with both advantages and disadvantages. Some inflammatory response is needed to create a new capillary bed in close proximity to the surface of the sensor in order to i) continuously deliver adequate oxygen and glucose and ii) create sufficient tissue ingrowth to anchor the implant and prevent motion artifact. On the other hand, inflammation is associated with invasion of tissue macrophages that have the ability to biodegrade many artificial biomaterials (some of which were, until recently, considered nonbiodegradable). When activated by a foreign body, tissue macrophages degranulate, releasing from their cytoplasmic myeloperoxidase system hypochlorite (bleach), $H_2O_2$ and other oxidant species. Both hypochlorite and $H_2O_2$ are known to break down a variety of polymers, including polyurethane, by a phenomenon referred to as environmental stress cracking. [Phillips et al., J. Biomat. Appl., 3:202-227 (1988); Stokes, J. Biomat. Appl. 3:228-259 (1988)]. Indeed, environmental stress cracking has been shown to limit the lifetime and performance of an enzyme-active polyurethane membrane stretched over the tip of a glucose sensor. [Updike et al., Am. Soc. Artificial Internal Organs, 40:157-163 (1994)].

Because both hypochlorite and $H_2O_2$ are short-lived chemical species in vivo, biodegradation will not occur if macrophages are kept a sufficient distance from the enzyme active membrane. The present invention contemplates the use of a bioprotective membrane that allows transport of glucose and oxygen but prevents the entry of inflammatory cells such as macrophages and foreign body giant cells. The bioprotective membrane is placed proximal to the angiogenic membrane. It may be simply placed adjacent to the angiogenic layer without adhering, or it may be attached with an adhesive material to the angiogenic layer, or it may be cast in place upon the angiogenic layer as described in Example 1. The devices of the present invention are not limited by the nature of the bioprotective layer. However, the bioprotective layer should be biostable for long periods of time (e.g., several years); the present invention contemplates the use of polymers including, but not limited to, polyurethane, polypropylene, polysulphone, polytetrafluoroethylene (PTFE), and poly(ethylene terephthalate) (PET).

Figure 4A:
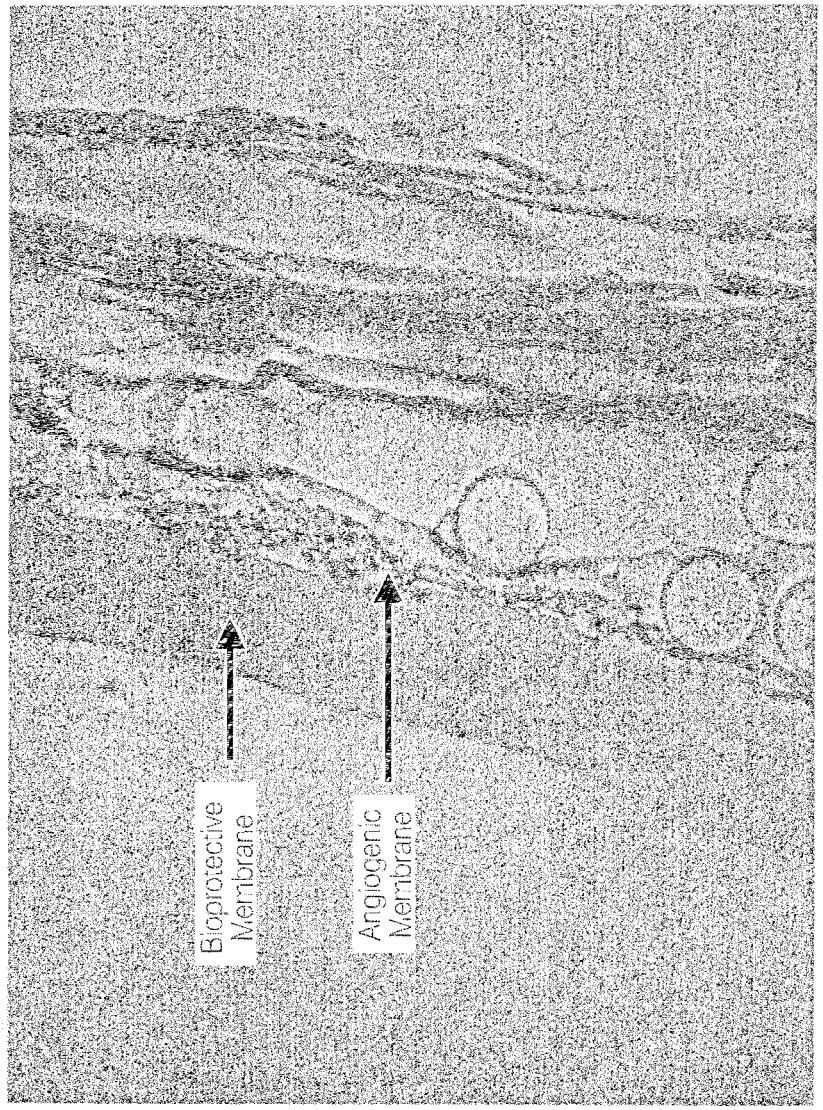
FIG. 4A is a photograph of an intact composite bioprotective/angiogenic membrane after implantation in a dog for 137 days.
Figure 4B:
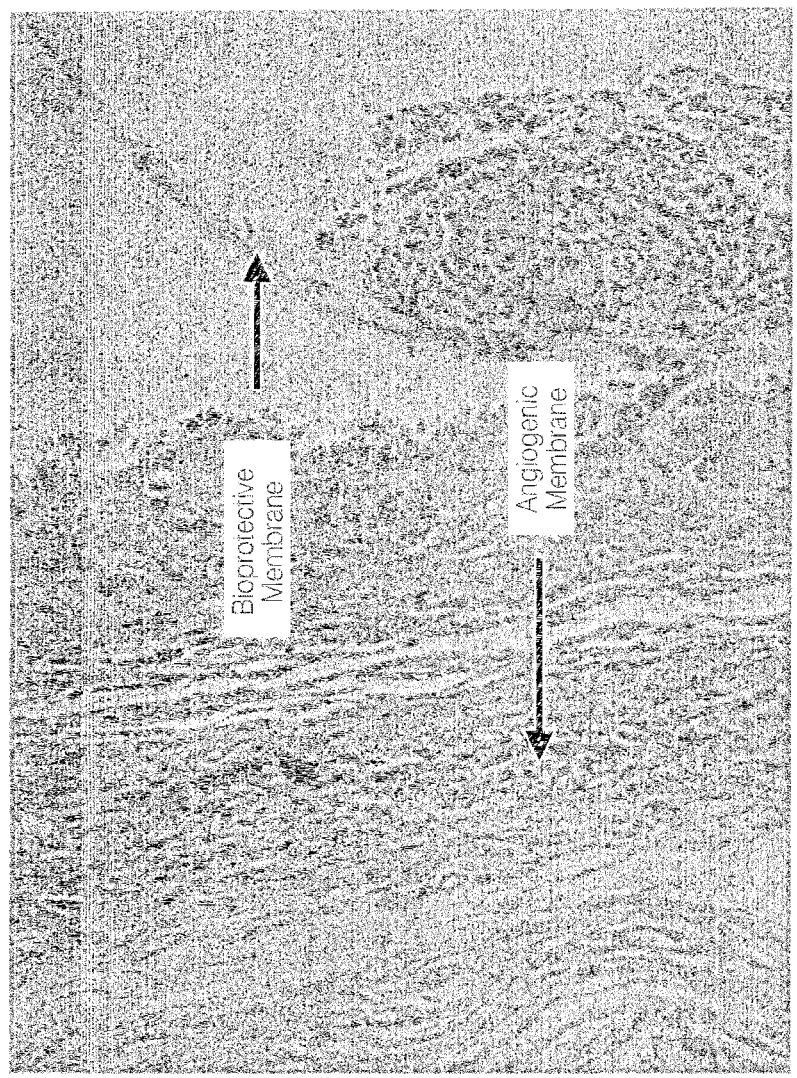
FIG. 4B is a photograph of a delaminated ePTFE bilayer membrane after implantation in a dog for 125 days.

The bioprotective membrane and the angiogenic layer may be combined into a single bilayer membrane as more fully described in Example 1. The active angiogenic function of the combined membrane is based on the presentation of the ePTFE side of the membrane to the reactive cells of the foreign body capsule and further to the response of the tissue to the microstructure of the ePTFE. This bioprotective/angiogenic membrane is unique in that the membrane does not delaminate as has been observed with other commercially available membranes (see FIG. 4A as compared with FIG. 4B). This is desirable for an implantable device to assure accurate measurement of analyte over long periods of time. Although the physical structure of the ePTFE represents a preferred embodiment, many other combinations of materials that provide the same function as the membrane of Example 1 could be utilized. For example, the ePTFE could be replaced by other fine fibrous materials. In particular, polymers such as spun polyolefin or non-organic materials such as mineral or glass fibers may be useful. Likewise, the polyurethane bioprotective layer of Example 1, which includes a biostable urethane and polyvinylpyrrolidone (PVP), could be replaced by polymers able to pass analyte while blocking macrophages and mechanically retaining the fine fibrous material presented to the reactive cells of the foreign body capsule.

C. Sensing Membrane

The present invention contemplates membranes impregnated with enzyme. It is not intended that the present invention be limited by the nature of the enzyme membrane. The sensing membrane of a preferred embodiment is depicted in FIG. 1C as being a single, homogeneous structure. However, in preferred embodiments, the sensing membrane includes a plurality of distinct layers. In a particularly preferred embodiment, the sensing membrane includes the following four layers (in succession from the bioprotective membrane to the layer most proximal to the electrodes): i) a resistance layer; ii) an enzyme layer; iii) an interference layer; and iv) an electrolyte layer.

Resistance Layer

There is a molar excess of glucose relative to the amount of oxygen in samples of blood. Indeed, for every free oxygen molecule in extracellular fluid, there are typically more than 100 glucose molecules present [Updike et al., Diabetes Care 5:207-21 (1982)]. However, an immobilized enzyme-based sensor using oxygen ($O_2$) as cofactor must be supplied with oxygen in non-rate-limiting excess in order to respond linearly to changes in glucose concentration while not responding to changes in oxygen tension. More specifically, when a glucose-monitoring reaction is oxygen-limited, linearity is not achieved above minimal concentrations of glucose. Without a semipermeable membrane over the enzyme layer, linear response to glucose levels can be obtained only up to about 40 mg/dL; however, in a clinical setting, linear response to glucose levels are desirable up to at least about 500 mg/dL.

The resistance layer includes a semipermeable membrane that controls the flux of oxygen and glucose to the underlying enzyme layer (i.e., limits the flux of glucose), rendering the necessary supply of oxygen in non-rate-limiting excess. As a result, the upper limit of linearity of glucose measurement is extended to a much higher value than that which could be achieved without the resistance layer. The devices of the present invention contemplate resistance layers comprising polymer membranes with oxygen-to-glucose permeability ratios of approximately 200:1; as a result, one-dimensional reactant diffusion is adequate to provide excess oxygen at all reasonable glucose and oxygen concentrations found in the subcutaneous matrix [Rhodes et al., Anal. Chem., 66:1520-1529 (1994)].

In preferred embodiments, the resistance layer has a thickness of less than about 45 µm, more preferably in the range of about 15 to about 40 µm, and most preferably in the range of about 20 to about 35 µm.

The resistance layer is desirably constructed of a mixture of hydrophobic and hydrophilic polyurethanes.

Enzyme Layer

In addition to glucose oxidase, the present invention contemplates the use of a membrane layer impregnated with other oxidases, e.g., galactose oxidase, uricase. For an enzyme-based electrochemical glucose sensor to perform well, the sensor's response must, neither be limited by enzyme activity nor cofactor concentration. Because enzymes, including the very robust glucose oxidase, are subject to deactivation as a function of ambient conditions, this behavior needs to be accounted for in constructing sensors for long-term use.

Excess glucose oxidase loading is required for long sensor life. When excess glucose oxidase is used, up to 1.5 years of performance may be possible from the glucose-monitoring devices contemplated by the present invention.

In one preferred embodiment, the enzyme layer includes a polyurethane latex.

Interference Layer

The interference layer includes a thin, hydrophobic membrane that is non-swellable and restricts diffusion of low molecular weight species. The interference layer is permeable to relatively low molecular weight substances, such as hydrogen peroxide, but restricts the passage of higher molecular weight substances, including glucose and ascorbic acid. The interference layer serves to allow analytes and other substances that are to be measured by the electrodes to pass through, while preventing passage of other substances.

Preferred materials from which the interference layer can be made include polyurethanes. In one desired embodiment, the interference layer includes an aliphatic polyetherurethane.

The interference layer has a preferred thickness of less than about 5 μm, more preferably in the range of about 0.1 to about 5 μm and most preferably in the range of about 0.5 to about 3 μm. Thicker membranes also may be useful, but thinner membranes are preferred because they have a lower impact on the rate of diffusion of hydrogen peroxide from the enzyme membrane to the electrodes.

Electrolyte Layer

To ensure electrochemical reaction, the electrolyte layer comprises a semipermeable coating that maintains hydrophilicity at the electrode region of the sensor interface. The electrolyte layer enhances the stability of the interference layer of the present invention by protecting and supporting the membrane that makes up the interference layer. Furthermore, the electrolyte layer assists in stabilizing operation of the device by overcoming electrode start-up problems and drifting problems caused by inadequate electrolyte. The buffered electrolyte solution contained in the electrolyte layer also protects against pH-mediated damage that may result from the formation of a large pH gradient between the hydrophobic interference layer and the electrode (or electrodes) due to the electrochemical activity of the electrode.

Preferably, the coating includes a flexible, water-swellable, substantially solid gel-like film having a "dry film" thickness of about 2.5 μm to about 12.5 μm, preferably about 6.0 μm. "Dry film" thickness refers to the thickness of a cured film cast from a coating formulation onto the surface of the membrane by standard coating techniques. The coating formulation includes a premix of film-forming polymers and a crosslinking agent and is curable upon the application of moderate heat.

Suitable coatings are formed of a curable copolymer of a urethane polymer and a hydrophilic film-forming polymer. Particularly preferred coatings are formed of a polyurethane polymer having anionic carboxylate functional groups and non-ionic hydrophilic polyether segments, which is crosslinked in the present of polyvinylpyrrolidone and cured at a moderate temperature of about 50° C.

Particularly suitable for this purpose are aqueous dispersions of fully reacted colloidal polyurethane polymers having cross-linkable carboxyl functionality (e.g., BAYBOND®; Mobay Corporation, Pittsburgh, Pa.). These polymers are supplied in dispersion grades having a polycarbonate-polyurethane backbone containing carboxylate groups identified as XW-121 and XW-123; and a polyester-polyurethane backbone containing carboxylate groups, identified as XW-110-2. Particularly preferred is BAYBOND® 123, an aqueous anionic dispersion of an aliphate polycarbonate urethane polymer, sold as a 35 weight percent solution in water and co-solvent N-methyl-2-pyrrolidone.

Polyvinylpyrrolidone is also particularly preferred as a hydrophilic water-soluble polymer and is available commercially in a range of viscosity grades and average molecular weights ranging from about 18,000 to about 500,000, under the PVP K® homopolymer series by BASF Wyandotte (Parsippany, N.J.) and by GAF Corporation (New York, N.Y.). Particularly preferred is the homopolymer having an average molecular weight of about 360,000, identified as PVP-K90 (BASF Wyandotte). Also suitable are hydrophilic, film-forming copolymers of N-vinylpyrrolidone, such as a copolymer of N-vinylpyrrolidone and vinyl acetate, a copolymer of N-vinylpyrrolidone, ethylmethacrylate and methacrylic acid monomers, and the like.

The polyurethane polymer is crosslinked in the presence of the polyvinylpyrrolidone by preparing a premix of the polymers and adding a cross-linking agent just prior to the production of the membrane. Suitable cross-linking agents can be carbodiimides, epoxides and melamine/formaldehyde resins. Carbodiimide is preferred, and a preferred carbodiimide crosslinker is UCARLNK® XL-25 (Union Carbide, Chicago, Ill.).

The flexibility and hardness of the coating can be varied as desired by varying the dry weight solids of the components in the coating formulation. The term "dry weight solids" refers to the dry weight percent based on the total coating composition after the time the crosslinker is included. A preferred useful coating formulation can contain about 6 to about 20 dry weight percent, preferably about 8 dry weight percent, of polyvinylpyrrolidone; about 3 to about 10 dry weight percent, preferably about 5 dry weight percent of cross-linking agent; and about 70 to about 91 weight percent, preferably about 87 weight percent of a polyurethane polymer, preferably a polycarbonate-polyurethane polymer. The reaction product of such a coating formulation is referred to herein as a water-swellable cross-linked matrix of polyurethane and PVP.

D. The Electrolyte Phase

The electrolyte phase is a free-fluid phase including a solution containing at least one compound, usually a soluble chloride salt that conducts electric current. The electrolyte phase flows over the electrodes (see FIG. 1C) and is in contact with the electrolyte layer of the enzyme membrane. The devices of the present invention contemplate the use of any suitable electrolyte solution, including standard, commercially available solutions.

Generally speaking, the electrolyte phase should have the same or less osmotic pressure than the sample being analyzed. In preferred embodiments of the present invention, the electrolyte phase includes saline.

E. The Electrode

The electrode assembly of this invention may also be used in the manner commonly employed in the making of amperometric measurements. The interstitial fluids containing the analyte to be measured is in contact with a reference electrode, e.g., silver/silver-chloride, and the anode and cathode of this invention, which are preferably formed of platinum. In the preferred embodiment, the electrodes are connected to a circuit board in the body of the sensor, the current is read and the information is radiotransmitted to a receiver. The invention is not limited to this preferred embodiment. Indeed the membranes of the present invention could be used with any form of implantable sensor and adapted to the particular features of the sensor by one skilled in the art.

The ability of the present device electrode assembly to accurately measure the concentration of substances such as glucose over a broad range of concentrations enables the rapid and accurate determination of the concentration of those substances. That information can be employed in the study and control of metabolic disorders including diabetes.

IV. SENSOR IMPLANTATION AND RADIOTELEMETRIC OUTPUT

Long-term sensor performance is best achieved, and transcutaneous bacterial infection is eliminated, with implanted devices capable of radiotelemetric output. The present invention contemplates the use of radiotelemetry to provide data regarding blood glucose levels, trends, and the like. The term "radiotelemetry" refers to the transmission by radio waves of the data recorded by the implanted device to an ex vivo recording station (e.g., a computer), where the data is recorded and, if desired, further processed.

Although totally implanted glucose sensors of three month lifetime, with radiotelemetric output, have been tested in animal models at intravenous sites [see, e.g. Armour et al., Diabetes, 39:1519-1526 (1990)], subcutaneous implantation is the preferred mode of implantation [see, e.g., Gilligan et al., Diabetes Care 17:882-887 (1994)]. The subcutaneous site has the advantage of lowering the risk for thrombophlebitis with hematogenous spread of infection and also lowers the risk of venous thrombosis with pulmonary embolism. In addition, subcutaneous placement is technically easier and more cost-effective than intravenous placement, as it may be performed under local anesthesia by a non-surgeon health care provider in an outpatient setting.

Preferably, the radiotelemetry devices contemplated for use in conjunction with the present invention possess features including small package size, adequate battery life, acceptable noise-free transmission range, freedom from electrical interference, and easy data collection and processing. Radiotelemetry provides several advantages, one of the most important of which is the ability of an implanted device to measure analyte levels in a sealed-off, sterile environment.

The present invention is not limited by the nature of the radiotelemetry equipment or methods for its use. Indeed, commercially available equipment can be modified for use with the devices of the present invention (e.g., devices manufactured by Data Sciences). Similarly, custom-designed radiotelemetry devices like those reported in the literature can be used in conjunction with the implantable analyte-measuring devices of the present invention [see, e.g., McKean and Gough, IEEE Trans. Biomed. Eng. 35:526-532 (1988); Shichiri et al., Diabetes Care 9:298-301 (1986); and Shults et al., IEEE Trans. Biomed. Eng. 41:937-942 (1994)]. In a preferred embodiment, transmitters are programmed with an external magnet to transmit at 0.5 or 5-minute intervals, depending on the need of the subject; presently, battery lifetimes at transmission intervals of 5 minutes are approximately up to 1.5 years.

V. EXPERIMENTAL

The following examples serve to illustrate certain preferred embodiments and aspects of the present invention and are not to be construed as limiting the scope thereof.

In the preceding description and the experimental disclosure which follows, the following abbreviations apply: Eq and Eqs (equivalents); mEq (milliequivalents); M (molar); mM (millimolar) $\mu$M (micromolar); N (Normal); mol (moles); mmol (millimoles); $\mu$mol (micromoles); nmol (nanomoles); g (grams); mg (milligrams); $\mu$g (micrograms); Kg (kilograms); L (liters); mL (milliliters); dL (deciliters); $\mu$L (microliters); cm (centimeters); mm (millimeters); $\mu$m (micrometers); nm (nanometers); h and hr (hours); min. (minutes); s and sec. (seconds); ° C. (degrees Centigrade); Astor Wax (Titusville, Pa.); BASF Wyandotte Corporation (Parsippany, N.J.); Data Sciences, Inc. (St. Paul, Minn.); DuPont (DuPont Co., Wilmington, Del.); Exxon Chemical (Houston, Tex.); GAF Corporation (New York, N.Y.); Markwell Medical (Racine, Wis.); Meadox Medical, Inc. (Oakland, N.J.); Mobay (Mobay Corporation, Pittsburgh, Pa.); Sandoz (East Hanover, N.J.); and Union Carbide (Union Carbide Corporation; Chicago, Ill.).

Example 1

Preparation of Composite Membrane of the Present Invention

The angiogenic layer may be an ePTFE filtration membrane (Zefluor™, 3.0 $\mu$m P5PI001, Pall Gelman, Ann Arbor, Mich.) and the bioprotective membrane (C30P) may then be coated on the angiogenic layer. For example, the C30P coating solution was prepared by placing approximately 706 gm of dimethylacetamide (DMAC) into a 3 L stainless steel bowl to which a polycarbonateurethane solution (1325 g, Chronoflex AR 25% solids in DMAC and 5100 cp) and polyvinylpyrrolidone (125 g, Plasdone K-90D) were added. The bowl was then fitted to a planetary mixer with a paddle type blade and the contents were stirred for 1 hour at room temperature. This solution was then coated on the ePTFE filtration membrane by knife-edge drawn at a gap of 0.006" and dried at 60° C. for 24 hours.

Alternatively, the C30P solution prepared above can be coated onto a PET release liner using a knife over roll coating machine. This material is then dried at 305° F. for approximately 2 minutes. Next, the Zefluor™ is immersed in 50:50 (w/v) mixture of tetrahydrofuran/DMAC and then placed upon the coated polyurethane polyvinylpyrrolidone material. Light pressure atop the assembly intimately embeds the ePTFE into the C30P layer. The membrane is then dried at 60° C. for 24 hours.

Example 2

Preparation of the Sensing Membrane

The sensing membrane includes a resistance layer, an enzyme layer, an interference layer and an electrolyte layer. The resistance layer was prepared by placing approximately 281 gm of DMAC into a 3 L stainless steel bowl to which a solution of polyetherurethaneurea (344 gm of Chronothane H, 29,750 cp at 25% solids in DMAC) was added. To this mixture was added another polyetherurethaneurea (312 gm, Chronothane 1020, 6275 cp at 25% solids in DMAC). The bowl was fitted to a planetary mixer with a paddle type blade and the contents were stirred for 30 minutes at room temperature. The resistance layer coating solution produced is coated onto a PET release liner (Douglas Hansen Co., Inc. Minneapolis, Minn.) using a knife over roll set at a 0.012" gap. This film is then dried at 305° F.

The enzyme layer was prepared by placing 304 gm polyurethane latex (Bayhydrol 140AQ, Bayer, Pittsburgh, Pa.) into a 3 L stainless steel bowl to which 51 gm of pyrogen free water and 5.85 gm of glucose oxidase (Sigma type VII from *Aspergillus niger*) is added. The bowl was then fitted to a planetary mixer with a whisk type blade and the mixture was stirred for 15 minutes. Approximately 24 hr prior to coating, a solution of glutaraldehyde (15.4 ml of a 2.5% solution in pyrogen free water) and 14 ml of pyrogen free water was added to the mixture. The solution was mixed by inverting a capped glass bottle by hand for about 3 minutes at room temperature. This mixture was then coated over the resistance layer with a #10 Mayer rod and dried above room temperature preferably at about 50° C.

The interference layer was prepared by placing 187 gm of tetrahydrofuran into a 500 ml glass bottle to which an 18.7 gm aliphatic polyetherurethane (Tecoflex SG-85A, Thermedics Inc., Woburn, Mass.) was added. The bottle was placed onto a roller at approximately 3 rpm within an oven set at 37° C. The mixture was allowed to roll for 24 hr. This mixture was coated over the dried enzyme layer using a flexible knife and dried above room temperature, preferably at about 50° C.

The electrolyte layer was prepared by placing 388 gm of polyurethane latex (Bayhydrol 123, Bayer, Pittsburgh, Pa. in a 3 L stainless steel bowl to which 125 gm of pyrogen free water and 12.5 gm polyvinylpyrrolidone (Plasdone K-90D) was added. The bowl was then fitted to a planetary mixer with a paddle type blade and stirred for 1 hr at room temperature. Within 30 minutes of coating, approximately 13.1 ml of carbodiimide (UCARLNK) was added and the solution was mixed by inverting a capped polyethylene jar by hand for about 3 min at room temperature. This mixture was coated over the dried interference layer with a #10 Mayer rod and dried above room temperature preferably at about 50° C.

In order to affix this multi-region membrane to a sensor head, it is first placed into phosphate buffer (pH 7.4) for about 2 minutes. It is then stretched over the nonconductive body of sensor head and affixed into place with an o-ring.

Example 3

In Vivo Evaluation of Glucose Measuring Devices Including the Biointerface Membranes of the Present Invention In vivo sensor function was determined by correlating the sensor output to blood glucose values derived from an external blood glucose meter. We have found that non-diabetic dogs do not experience rapid blood glucose changes, even after ingestion of a high sugar meal. Thus, a 10% dextrose solution was infused into the sensor-implanted dog. A second catheter is placed in the opposite leg for the purpose of blood collection. The implanted sensor was programmed to transmit at 30-second intervals using a pulsed electromagnet. A dextrose solution was infused at a rate of 9.3 ml/minute for the first 25 minutes, 3.5 ml/minute for the next 20 minutes, 1.5 ml/minute for the next 20 minutes, and then the infusion pump was powered off. Blood glucose values were measured in duplicate every five minutes on a blood glucose meter (LXN Inc., San Diego, Calif.) for the duration of the study. A computer collected the sensor output. The data was then compiled and graphed in a spreadsheet, time aligned, and time shifted until an optimal R-squared value was achieved. The R-squared value reflects how well the sensor tracks with the blood glucose values.

To test the importance of the composite membrane of the invention described in Example 1, implantable glucose sensors including the composite and sensing membranes of the present invention were implanted into dogs in the subcutaneous tissues and monitored for glucose response on a weekly basis. Control devices including only a bioprotective C30P layer ("Control") were compared with devices including both a bioprotective and an angiogenic layer ("Test"), which corresponded to the composite bioprotective/angiogenic membrane of the device of the present invention described in Example 1.

Figure 3:
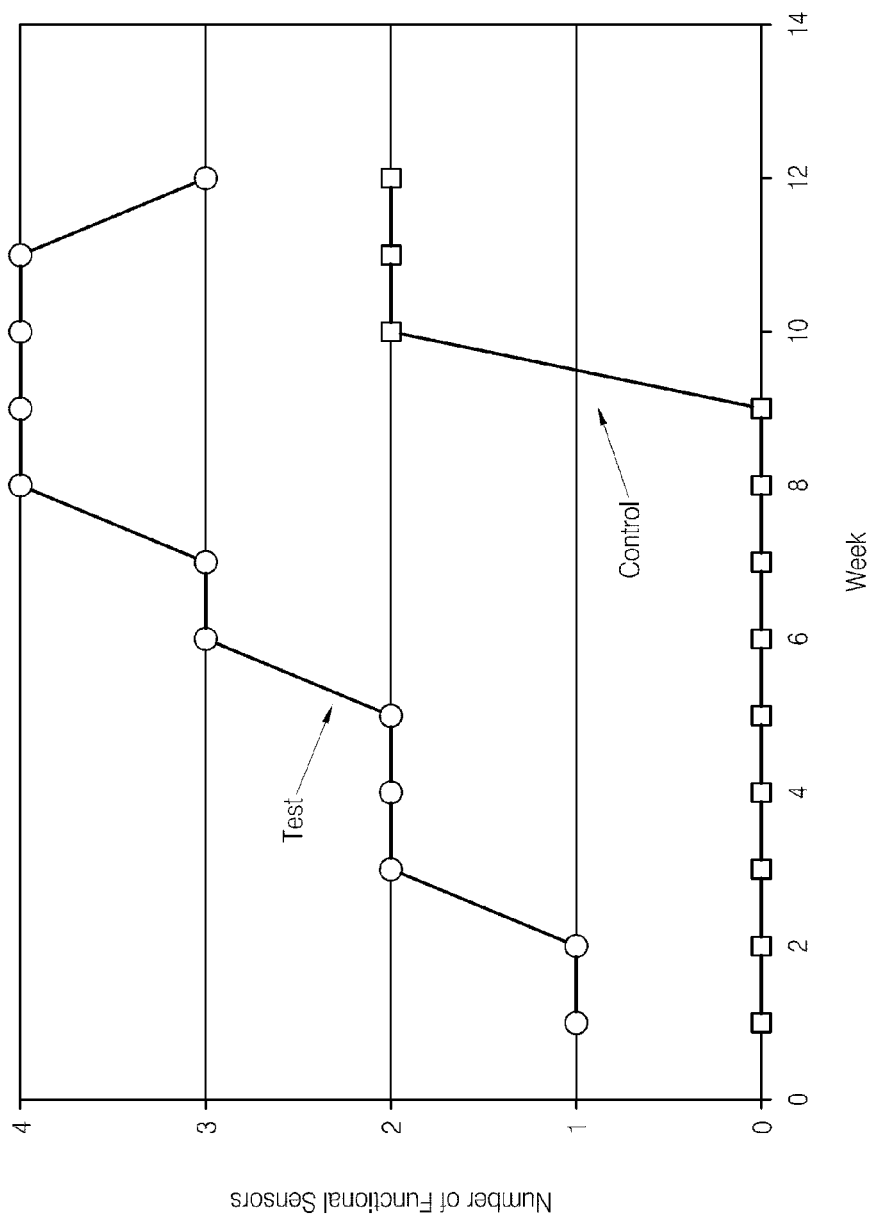
FIG. 3 is a graphical representation of the number of functional sensors versus time (i.e. weeks) comparing control devices including only a cell-impermeable domain ("Control"), with devices including a cell-impermeable domain and a barrier-cell domain ("Test").

Four devices from each condition were implanted subcutaneously in the ventral abdomen of normal dogs. On a weekly basis, the dogs were infused with glucose as described above in order to increase their blood glucose levels from about 120 mg/dl to about 300 mg/dl. Blood glucose values were determined with a LXN blood glucose meter at 5-minute intervals. Sensor values were transmitted at 0.5-minute intervals. Regression analysis was done between blood glucose values and the nearest sensor value within one minute. Devices with an R-squared value greater than 0.5 were considered functional. FIG. 3 shows, for each condition, the cumulative number of functional devices over the 12-week period of the study. The Test devices performed better than the Control devices over the entire 12 weeks of the study. All of the test devices were functional by week 8. In contrast, none of the control devices were functional until week 10, after which 2 were functional for the remaining 2 weeks. The data shows that the use of the inventive biointerface membrane enables the function of implantable glucose sensors.

The description and experimental materials presented above are intended to be illustrative of the present invention while not limiting the scope thereof. It will be apparent to those skilled in the art that variations and modifications can be made without departing from the spirit and scope of the present invention.

What is claimed is:

1. An implantable optical-based continuous glucose sensing device, the device comprising:
   a radiation source;
   an optical sensor configured to measure a signal indicative of glucose concentration;
   sensor electronics operably connected to the sensor;
   a housing configured to receive the radiation source, the optical sensor, and the sensor electronics; and
   a membrane configured to interface with tissue; wherein the membrane comprises an outer surface and an inner surface, wherein the outer surface of the membrane is more distal to the sensor than the inner surface of the membrane, wherein the outer surface of the membrane comprises partial metallization.

2. The device of claim 1, wherein the metallization comprises platinum.

3. The device of claim 1, wherein the metallization comprises vacuum deposited metal.

4. The device of claim 1, further comprising fluorescence sensing molecules configured to detect a presence of glucose.

5. The device of claim 1, wherein the membrane is configured to protect the sensor from in vivo environmental conditions.

* * * * *

UNITED STATES PATENT AND TRADEMARK OFFICE
CERTIFICATE OF CORRECTION

PATENT NO.       : 8,923,947 B2                           Page 1 of 3
APPLICATION NO.  : 13/949088
DATED            : December 30, 2014
INVENTOR(S)      : Mark C. Shults It is certified that error appears in the above-identified patent and that said Letters Patent is hereby corrected as shown below:

On the Title Page

Page 1 (item 74, Attorney) at line 2, change "Bear" to --Bear, LLP--.

In column 1 (page 5, item 56) at line 53, Under Other Publications, change "hypoglycaemic" to --hypoglycemic--.

In column 2 (page 5, item 56) at line 3, Under Other Publications, change "Thechnol." to --Technol.--.

In column 2 (page 5, item 56) at line 8, Under Other Publications, change "Senso" to --Sensor--.

In column 2 (page 5, item 56) at line 26, Under Other Publications, change "535-41." to --S35-41--.

In column 2 (page 5, item 56) at line 66, Under Other Publications, change "basedon" to --based--.

In column 1 (page 6, item 56) at line 21, Under Other Publications, change "reliablity" to --reliability--.

In column 1 (page 6, item 56) at line 34, Under Other Publications, change "Enzymlology," to --Enzymology,--.

In column 1 (page 6, item 56) at line 48, Under Other Publications, change "artifical" to --artificial--.

In column 1 (page 7, item 56) at line 39, Under Other Publications, change "Technol" to --Technol.--.

In column 2 (page 7, item 56) at line 1, Under Other Publications, change "inactiviation" to --inactivation--.

Signed and Sealed this
Eleventh Day of August, 2015

Michelle K. Lee
*Director of the United States Patent and Trademark Office*

CERTIFICATE OF CORRECTION (continued)
U.S. Pat. No. 8,923,947 B2

In column 2 (page 7, item 56) at line 18, Under Other Publications, change "patents" to --patients--.

In column 2 (page 7, item 56) at line 20, Under Other Publications, change "et al" to --et al.,--.

In column 2 (page 7, item 56) at line 54, Under Other Publications, change "Annu Annu" to --Annu--.

In column 1 (page 8, item 56) at line 5, Under Other Publications, change "Aniodic" to --Anodic--.

In column 2 (page 8, item 56) at line 12, Under Other Publications, change "activitiy," to --activity,--.

In column 2 (page 8, item 56) at line 26, Under Other Publications, change "Biosensors& Beioelectronics," to --Biosensors & Bioelectronics,--.

In column 2 (page 8, item 56) at line 40, Under Other Publications, change "valication" to --validation--.

In column 2 (page 8, item 56) at line 41, Under Other Publications, change "glucoseiunsulin interaaction in tyhpe 1" to --glucose insulin interaction in type 1--.

In column 2 (page 8, item 56) at line 59, Under Other Publications, change "Electronanalysis" to --Electroanalysis--.

In column 1 (page 9, item 56) at line 18, Under Other Publications, change "amperometeric" to --amperometric--.

In column 1 (page 9, item 56) at line 26, Under Other Publications, change "Thechnol." to --Technol.--.

In column 1 (page 9, item 56) at line 61, Under Other Publications, change "termistor" to --thermistor--.

In column 1 (page 9, item 56) at line 62, Under Other Publications, change "metobolites," to --metabolites,--.

In column 1 (page 9, item 56) at line 64, Under Other Publications, change "cholesteral and cholesteral" to --cholesterol and cholesterol--.

In column 2 (page 9, item 56) at line 53, Under Other Publications, change "Bromedical" to --Biomedical--.

In column 2 (page 10, item 56) at line 15, Under Other Publications, change "Membran," to --Membrane,--.

In column 1 (page 11, item 56) at line 8, Under Other Publications, change "Thechnol." to --Technol.--.

CERTIFICATE OF CORRECTION (continued)
U.S. Pat. No. 8,923,947 B2

In column 1 (page 11, item 56) at line 38, Under Other Publications, change "Membrance" to --Membrane--.

In the Specification

In column 1 at lines 19-22, Change "6,862,465, which is a continuation-in-part of U.S. application Ser. No. 09/447,227, filed Nov. 22, 1999, which is a divisional of U.S. application Ser. No. 08/811,473, filed Mar. 4, 1997, now U.S. Pat. No. 6,001,067." to --6,862,465.--.

In column 6 at lines 10-11, Change "Biologies" to --Biologie--.

In column 7 at line 2, Change "conconavalin" to --concanavalin--.

In column 9 at line 25, Change "(Shanker" to --(Shankar--.

In column 9 at line 45, Change "England)," to --England).--.

In column 10 at line 63, Change "(TEFLON/®;" to --(TEFLON®;--.

In column 11 at line 30, Change "radioopaque." to --radiopaque.--.

In column 15 at line 65, Change "aliphate" to --aliphatic--.